United States Patent [19]
Uchimura et al.

[11] Patent Number: 6,037,159
[45] Date of Patent: Mar. 14, 2000

[54] POLYPEPTIDE OF N-ACETYLGLUCOSAMINE-6-O-SULFOTRANSFERASE AND DNA ENCODING THE SAME

[75] Inventors: Kenji Uchimura, Nagoya; Hideki Muramatsu, Shizuoka-ken; Kenji Kadomatsu, Nagoya; Reiji Kannagi, Nagoya; Osami Habuchi, Nagoya; Takashi Muramatsu, Nagoya, all of Japan

[73] Assignee: Seikagaku Corporation, Tokyo, Japan

[21] Appl. No.: 09/263,023

[22] Filed: Mar. 5, 1999

[30]     Foreign Application Priority Data

Mar. 5, 1998 [JP] Japan .................................. 10-054007
Jun. 24, 1998 [JP] Japan .................................. 10-177844

[51] Int. Cl.$^7$ ...................................................... C12N 9/10
[52] U.S. Cl. ........................... 435/193; 435/69.1; 435/72; 435/183; 435/252.1
[58] Field of Search .................................. 435/69.1, 193, 435/72, 183, 252.1

[56]         References Cited

PUBLICATIONS

Yuichiro Yasumoto, et al., Characterization of a rat liver Golgi sulphotransferase responsible for the 6–O–sulphation of N–acetylglucosamine residues in β–linkage to mannose: role in assembly of sialyl–galactosyl–N–acetylglucosamine 6–sulphate sequence of N–linked oligosaccharides, Biochem. J. (1996) 319,209–216.

Sophie Degroote, et al., Characterization of an N–Acetylglucosamine–6–O–sulfotransferase from Human Respiratory Mucosa Active on Mucin Carbohydrate Chains, The Journal of Biological Chemistry, vol. 272, No. 47, Issue of Nov. 21, pp. 29493–29501, 1997.

Kendra G. Bowman, et al., Identification of an N–acetylglucosamine–6–O–sulfotransferase activity specific to lymphoid tissue: an enzyme with a possible role in lymphocyte homing, Chemistry & Biology Aug. 1998, 5:447–460.

Kenji Uchimura, et al., Human N–Acetylglucosamine–6–O–Sulfotransferase Involved in the Biosynthesis of 6–Sulfo Sialyl Lewis X: Molecular Cloning, Chromosomal Mapping, and Expression in Various Organs and Tumor Cells, J. Biochem, 124, 670–678 (1998).

Kenji Uchimura, et al., Molecular Cloning and Characterization of an N–Acetylglucosamine–6–O–sulfotransferase, The Journal of Biological Chemistry, vol. 273, No. 35, Issue of Aug. 28, pp. 22577–22583, 1998.

Kiyoshi Nakazawa, et al., Glycosyltransferase and Sulfotransferase Activities in Chick Corneal Stromal Cells before and after in Vitro Culture, Archives of Biochemistry and Biophysics, vol. 359, No. 2, Nov. 14, pp. 269–282, 1998.

*Primary Examiner*—Rebecca E. Prouty
*Assistant Examiner*—Richard Hutson
*Attorney, Agent, or Firm*—Knobbe, Martens, Olson & Bear, LLP

[57]         ABSTRACT

A polypeptide of N-acetylglucosamine-6-O-sulfotransferase and a DNA encoding the peptide are provided. The polypeptide is (a) or (b) below:

(a) a polypeptide consisting of an amino acid sequence represented by SEQ ID NO: 2; or (b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

GlcNAcβ1-3Galβ1-4GlcNAc         (I)

wherein GlcNAc represents an N-acetylglucosamine residue, Gal represents a galactose residue, β1-3 represents a β1-3 glycosidic linkage, and β1-4 represents a β1-4 glycosidic linkage.

13 Claims, 8 Drawing Sheets

SEQUENCE LISTING

<160> NUMBER OF SEQ ID NOS: 10

<210> SEQ ID NO 1
<211> LENGTH: 2150
<212> TYPE: DNA
<213> ORGANISM: Mus musculus
<220> FEATURE:
<221> NAME/KEY: CDS
<222> LOCATION: (470)...(1918)

<400> SEQUENCE: 1

```
ggctagggca gcggagtctc gcggctccct cgaaggcttg gggaccccta gcagaagaga      60
accggagaga aaccgaggag agtgctagcc ggacagtccg ccggtcgggg atctggggac     120
gctccgaggc gcaccctccg ctccaggtcc ttctcggagc cgctgccatg ggagagccag     180
ccctgggcgc cggggaccag cagcctctgc cgccgcgccc gcctcggatc ggcggcccca     240
gtcccggcgc ccgcagccgg cctgcagcgt ccccctcctg ggctgcaggg ccgcctccgc     300
cgcgccgccg gccccggctg tgcctgtgat gagccgcagc tcgccgcgag ctctgccccc     360
cggtgcgctt ccccggccgc tgccggccgc gcctgccgcc gtgcagcggg ccctgctccc     420
gccgtggccc cggcgcgcag gacgccgctg gcctgcgtcc ccgctcggg atg aag gta    478
                                                        Met Lys Val
                                                           1 ttt cgc agg aag gcg ctg gtg ctg tgc gcg ggc tat gca ctg cta ctg        526
Phe Arg Arg Lys Ala Leu Val Leu Cys Ala Gly Tyr Ala Leu Leu Leu
    5                  10                  15 gtg ctc acg atg ctc aac ctc ttg gac tac aag tgg cat aaa gag ccg        574
Val Leu Thr Met Leu Asn Leu Leu Asp Tyr Lys Trp His Lys Glu Pro
 20                  25                  30                  35 ctg cag cag tgc aac ccc gac ggg cct ctg ggt gcc gcg gta ggg gcg        622
Leu Gln Gln Cys Asn Pro Asp Gly Pro Leu Gly Ala Ala Val Gly Ala
                 40                  45                  50 gcc ggg gcc ggc tgg gga cgg ccg ggg tcg cct cct gca gcg cca ccc        670
Ala Gly Ala Gly Trp Gly Arg Pro Gly Ser Pro Pro Ala Ala Pro Pro
```

|  |  |
|---|---|
| cgc gct cac tct cgc atg gac ccc cgc acc ccg tac cgc cct cct gcc<br>Arg Ala His Ser Arg Met Asp Pro Arg Thr Pro Tyr Arg Pro Pro Ala<br>        70                         75                      80 | 718 |
| gcg ggc gtg ggg gca gtt ccc gca gcc gcg gct ggg agt gca gga gct<br>Ala Gly Val Gly Ala Val Pro Ala Ala Ala Ala Gly Ser Ala Gly Ala<br>85                       90                         95 | 766 |
| gcg gcc tct ctg ggc aat gct act cga ggc acc agg ggt gga ggg gac<br>Ala Ala Ser Leu Gly Asn Ala Thr Arg Gly Thr Arg Gly Gly Gly Asp<br>100                     105                   110                   115 | 814 |
| aag cgg cag ttg gtg tat gtg ttc acc acg tgg cgc tcg ggc tcg tcc<br>Lys Arg Gln Leu Val Tyr Val Phe Thr Thr Trp Arg Ser Gly Ser Ser<br>                     120                   125                   130 | 862 |
| ttc ttc ggt gag ctc ttc aac cag aac cct gag gtg ttc ttc ctc tat<br>Phe Phe Gly Glu Leu Phe Asn Gln Asn Pro Glu Val Phe Phe Leu Tyr<br>                  135                   140                   145 | 910 |
| gag cct gtg tgg cac gtg tgg caa aaa ctg tac ccc ggg gac gcc gtt<br>Glu Pro Val Trp His Val Trp Gln Lys Leu Tyr Pro Gly Asp Ala Val<br>         150                   155                   160 | 958 |
| tcc ctg cag ggg gca gcg cgg gac atg ctg agc gct ctc tac cgc tgc<br>Ser Leu Gln Gly Ala Ala Arg Asp Met Leu Ser Ala Leu Tyr Arg Cys<br>165                   170                   175 | 1006 |
| gat ctt tcg gtt ttc cag ctg tat agc ccc gca ggc agt ggg ggg cgc<br>Asp Leu Ser Val Phe Gln Leu Tyr Ser Pro Ala Gly Ser Gly Gly Arg<br>180                   185                   190                   195 | 1054 |
| aac ctc acc act ctg ggc atc ttt ggg gca gcc act aac aag gtg gta<br>Asn Leu Thr Thr Leu Gly Ile Phe Gly Ala Ala Thr Asn Lys Val Val<br>                    200                   205                   210 | 1102 |
| tgc tcc tcg cca ctc tgt cct gcc tac cgc aag gag gtc gtc gga ctg<br>Cys Ser Ser Pro Leu Cys Pro Ala Tyr Arg Lys Glu Val Val Gly Leu<br>               215                   220                   225 | 1150 |
| gtg gac gac cgc gtg tgc aaa aag tgc cca cct caa cgc ctg gca cgc<br>Val Asp Asp Arg Val Cys Lys Lys Cys Pro Pro Gln Arg Leu Ala Arg<br>         230                   235                   240 | 1198 |
| ttc gag gag gag tgt cgc aag tac cgc acg gtg gtt atc aag ggc gtg<br>Phe Glu Glu Glu Cys Arg Lys Tyr Arg Thr Val Val Ile Lys Gly Val<br>245                   250                   255 | 1246 |
| cgg gtc ttc gat gtg gct gtg ttg gcg ccg ctg ctt aaa gat cca gcc<br>Arg Val Phe Asp Val Ala Val Leu Ala Pro Leu Leu Lys Asp Pro Ala<br>260                   265                   270                   275 | 1294 |
| ttg gac ctc aag gtc atc cac cta gta cgt gat cct cgt gct gtt gcc<br>Leu Asp Leu Lys Val Ile His Leu Val Arg Asp Pro Arg Ala Val Ala<br>                    280                   285                   290 | 1342 |
| agc tcc cgc atc cgc tcg cgt cac ggc ctc atc cgg gaa agc cta cag<br>Ser Ser Arg Ile Arg Ser Arg His Gly Leu Ile Arg Glu Ser Leu Gln<br>               295                   300                   305 | 1390 |
| gtg gtg cga agc cgg gat cca aga gcc cac cgc atg ccc ttc ctg gag<br>Val Val Arg Ser Arg Asp Pro Arg Ala His Arg Met Pro Phe Leu Glu<br>         310                   315                   320 | 1438 |
| gct gct ggc cac aag ctt ggt gcc aag aag gag ggt atg ggt ggc cca<br>Ala Ala Gly His Lys Leu Gly Ala Lys Lys Glu Gly Met Gly Gly Pro<br>325                   330                   335 | 1486 |
| gca gac tac cac gct ctg ggt gca atg gag gtc atc tgc aac agt atg<br>Ala Asp Tyr His Ala Leu Gly Ala Met Glu Val Ile Cys Asn Ser Met<br>340                   345                   350                   355 | 1534 |
| gcc aag acg ctg caa aca gcc ctg cag cct cct gac tgg ctg cag gga<br>Ala Lys Thr Leu Gln Thr Ala Leu Gln Pro Pro Asp Trp Leu Gln Gly<br>                    360                   365                   370 | 1582 |
| cac tac ttg gtg gtg agg tac gag gat ctg gtg gga gac ccc gtt aag | 1630 |

| | | | | | | | | | | | | | | | |
|---|---|---|---|---|---|---|---|---|---|---|---|---|---|---|---|
| His | Tyr | Leu | Val | Val | Arg | Tyr | Glu | Asp | Leu | Val | Gly | Asp | Pro | Val | Lys |
| | | 375 | | | | | 380 | | | | | 385 | | | |

```
acc cta cgg agg gta tat gac ttt gtg ggg ctg ctg gtg agt ccc gaa   1678
Thr Leu Arg Arg Val Tyr Asp Phe Val Gly Leu Leu Val Ser Pro Glu
        390                 395                 400 atg gag cag ttt gcc ctg aac atg acc agt ggt tcg ggc tcc tcc tcc   1726
Met Glu Gln Phe Ala Leu Asn Met Thr Ser Gly Ser Gly Ser Ser Ser
405                 410                 415 aag cct ttc gtg gtg tca gct cgc aat gcc act cag gcc gcc aat gcc   1774
Lys Pro Phe Val Val Ser Ala Arg Asn Ala Thr Gln Ala Ala Asn Ala
420                 425                 430                 435 tgg cgg acc gcg ctc acc ttc cag cag atc aaa cag gtg gag gag ttt   1822
Trp Arg Thr Ala Leu Thr Phe Gln Gln Ile Lys Gln Val Glu Glu Phe
                440                 445                 450 tgc tac cag ccc atg gcc gtg ctg ggc tat gag cgg gtt aac agt cct   1870
Cys Tyr Gln Pro Met Ala Val Leu Gly Tyr Glu Arg Val Asn Ser Pro
            455                 460                 465 gag gag gtc aaa gac ctc agc aag acc ttg ctc agg aag ccc cgg ctt   1918
Glu Glu Val Lys Asp Leu Ser Lys Thr Leu Leu Arg Lys Pro Arg Leu
        470                 475                 480 tgagaagggt tcccaagaga tctgacactc tccggagaca cccacaaaaa ggatggtgtt   1978
gtgtttaaac aaacacagcc cagacccaag ctgaggaagc ccacatattc tattatagat   2038
atataatata aataaccaca caggcacttg ctgtcaacgt tttgagtcag tgcatttcaa   2098
ggaacagccc tcaactcaca cgacaaactt ctggccctcc aacaagacac ac           2150

<210> SEQ ID NO 2
<211> LENGTH: 483
<212> TYPE: PRT
<213> ORGANISM: Mus musculus

<400> SEQUENCE: 2

Met Lys Val Phe Arg Arg Lys Ala Leu Val Leu Cys Ala Gly Tyr Ala
1               5                   10                  15

Leu Leu Leu Val Leu Thr Met Leu Asn Leu Leu Asp Tyr Lys Trp His
                20                  25                  30

Lys Glu Pro Leu Gln Gln Cys Asn Pro Asp Gly Pro Leu Gly Ala Ala
            35                  40                  45

Val Gly Ala Ala Gly Ala Gly Trp Gly Arg Pro Gly Ser Pro Pro Ala
        50                  55                  60

Ala Pro Pro Arg Ala His Ser Arg Met Asp Pro Arg Thr Pro Tyr Arg
65                  70                  75                  80

Pro Pro Ala Ala Gly Val Gly Ala Val Pro Ala Ala Ala Ala Gly Ser
                85                  90                  95

Ala Gly Ala Ala Ala Ser Leu Gly Asn Ala Thr Arg Gly Thr Arg Gly
            100                 105                 110

Gly Gly Asp Lys Arg Gln Leu Val Tyr Val Phe Thr Thr Trp Arg Ser
        115                 120                 125

Gly Ser Ser Phe Phe Gly Glu Leu Phe Asn Gln Asn Pro Glu Val Phe
    130                 135                 140

Phe Leu Tyr Glu Pro Val Trp His Val Trp Gln Lys Leu Tyr Pro Gly
145                 150                 155                 160

Asp Ala Val Ser Leu Gln Gly Ala Ala Arg Asp Met Leu Ser Ala Leu
                165                 170                 175

Tyr Arg Cys Asp Leu Ser Val Phe Gln Leu Tyr Ser Pro Ala Gly Ser
            180                 185                 190
```

```
Gly Gly Arg Asn Leu Thr Thr Leu Gly Ile Phe Gly Ala Ala Thr Asn
            195                 200                 205

Lys Val Val Cys Ser Ser Pro Leu Cys Pro Ala Tyr Arg Lys Glu Val
    210                 215                 220

Val Gly Leu Val Asp Asp Arg Val Cys Lys Lys Cys Pro Pro Gln Arg
225                 230                 235                 240

Leu Ala Arg Phe Glu Glu Cys Arg Lys Tyr Arg Thr Val Val Ile
                245                 250                 255

Lys Gly Val Arg Val Phe Asp Val Ala Val Leu Ala Pro Leu Leu Lys
                260                 265                 270

Asp Pro Ala Leu Asp Leu Lys Val Ile His Leu Val Arg Asp Pro Arg
                275                 280                 285

Ala Val Ala Ser Ser Arg Ile Arg Ser Arg His Gly Leu Ile Arg Glu
                290                 295                 300

Ser Leu Gln Val Val Arg Ser Arg Asp Pro Arg Ala His Arg Met Pro
305                 310                 315                 320

Phe Leu Glu Ala Ala Gly His Lys Leu Gly Ala Lys Lys Glu Gly Met
                325                 330                 335

Gly Gly Pro Ala Asp Tyr His Ala Leu Gly Ala Met Glu Val Ile Cys
                340                 345                 350

Asn Ser Met Ala Lys Thr Leu Gln Thr Ala Leu Gln Pro Pro Asp Trp
                355                 360                 365

Leu Gln Gly His Tyr Leu Val Val Arg Tyr Glu Asp Leu Val Gly Asp
                370                 375                 380

Pro Val Lys Thr Leu Arg Arg Val Tyr Asp Phe Val Gly Leu Leu Val
385                 390                 395                 400

Ser Pro Glu Met Glu Gln Phe Ala Leu Asn Met Thr Ser Gly Ser Gly
                405                 410                 415

Ser Ser Ser Lys Pro Phe Val Val Ser Ala Arg Asn Ala Thr Gln Ala
                420                 425                 430

Ala Asn Ala Trp Arg Thr Ala Leu Thr Phe Gln Gln Ile Lys Gln Val
                435                 440                 445

Glu Glu Phe Cys Tyr Gln Pro Met Ala Val Leu Gly Tyr Glu Arg Val
    450                 455                 460

Asn Ser Pro Glu Glu Val Lys Asp Leu Ser Lys Thr Leu Leu Arg Lys
465                 470                 475                 480

Pro Arg Leu

<210> SEQ ID NO 3
<211> LENGTH: 2409
<212> TYPE: DNA
<213> ORGANISM: Homo sapiens
<220> FEATURE:
<221> NAME/KEY: CDS
<222> LOCATION: (390)...(1841)

<400> SEQUENCE: 3
cgaggaacga gtgacagccg acagtccgc cgggcggtga tccggggccg ctcccgggcg      60
cgccctcggc tccaggtcct acccggagcc gctgccatgg gagagccagc cttgggcgct     120
ggggaccagc cgccgcgccc gcctcggagt cgcggcccga gtcccggcgc cagcagccag     180
cccgctgcgt cccctttccccg ggctgcaggg ctgcctccgc cgcgccgccg gcccggattg    240
tgcctgtgat gagccgcagc ccgcagcgag ctctgccccc gggcgcgctc cctcggctgc     300
tccaggctgc gcctgcagcg cagccgcgtg ccctgctccc gcagtggccc cggcgcccag     360
```

-continued

| | |
|---|---|
| gacgccgctg gcccgcgtcc cctctcgga atg aag gtg ttc cgt agg aag gcg<br>                                      Met Lys Val Phe Arg Arg Lys Ala<br>                                        1               5 | 413 |
| ctg gtg ttg tgc gcg ggc tat gca ctg ctg ctg gtg ctc act atg ctc<br>Leu Val Leu Cys Ala Gly Tyr Ala Leu Leu Leu Val Leu Thr Met Leu<br>        10                  15                  20 | 461 |
| aac ctc ctg gac tac aag tgg cac aag gag ccg ctg cag cag tgc aac<br>Asn Leu Leu Asp Tyr Lys Trp His Lys Glu Pro Leu Gln Gln Cys Asn<br>25                  30                  35                  40 | 509 |
| ccc gat ggg ccg ctg ggt gcc gca gcg gga gca gcc gga ggc aag ctg<br>Pro Asp Gly Pro Leu Gly Ala Ala Ala Gly Ala Ala Gly Gly Lys Leu<br>                45                  50                  55 | 557 |
| ggg gcg ccc agg gcc gcc tcc ggc cgg gcc gcc ccg tgc tca tgc ccg<br>Gly Ala Pro Arg Ala Ala Ser Gly Arg Ala Ala Pro Cys Ser Cys Pro<br>            60                  65                  70 | 605 |
| ttt gga cct ccg cac tcc tta ccg ccc tcc cgc tgc cgc cgt cgg ggc<br>Phe Gly Pro Pro His Ser Leu Pro Pro Ser Arg Cys Arg Arg Arg Gly<br>        75                  80                  85 | 653 |
| gat act ctg cag ccg cgg cag gga tgg cgg ggg ttg cgg ccc ctc cag<br>Asp Thr Leu Gln Pro Arg Gln Gly Trp Arg Gly Leu Arg Pro Leu Gln<br>    90                  95                  100 | 701 |
| gca atg gca ctc ggg gca ccg gag ggc gtc ggg gac aag cgg cac tgg<br>Ala Met Ala Leu Gly Ala Pro Glu Gly Val Gly Asp Lys Arg His Trp<br>105                 110                 115                 120 | 749 |
| atg tac gtg ttc acc acg tgg cgc tct ggc tcg tcg ttc ttc ggc gag<br>Met Tyr Val Phe Thr Thr Trp Arg Ser Gly Ser Ser Phe Phe Gly Glu<br>                125                 130                 135 | 797 |
| cta ttc aac cag aat ccc gag gtg ttc ttt ctc tac gag cca gtg tgg<br>Leu Phe Asn Gln Asn Pro Glu Val Phe Phe Leu Tyr Glu Pro Val Trp<br>            140                 145                 150 | 845 |
| cat gta tgg caa aaa ctg tat ccg ggg gac gcc gtt tcc ctg cag ggg<br>His Val Trp Gln Lys Leu Tyr Pro Gly Asp Ala Val Ser Leu Gln Gly<br>        155                 160                 165 | 893 |
| gca gcg cgg gac atg ctg agc gct ctt tac cgc tgc gac ctc tct gtc<br>Ala Ala Arg Asp Met Leu Ser Ala Leu Tyr Arg Cys Asp Leu Ser Val<br>    170                 175                 180 | 941 |
| ttc cag ttg tat agc ccc gcg ggc agc ggg ggg cgc aac ctc acc acg<br>Phe Gln Leu Tyr Ser Pro Ala Gly Ser Gly Gly Arg Asn Leu Thr Thr<br>185                 190                 195                 200 | 989 |
| ctg ggc atc ttc ggc gca gcc acc aac aag gtg gtg tgc tcg tca cca<br>Leu Gly Ile Phe Gly Ala Ala Thr Asn Lys Val Val Cys Ser Ser Pro<br>                205                 210                 215 | 1037 |
| ctc tgc ccc gcc tac cgc aag gag gtc gtg ggg ttg gtg gac gac cgc<br>Leu Cys Pro Ala Tyr Arg Lys Glu Val Val Gly Leu Val Asp Asp Arg<br>            220                 225                 230 | 1085 |
| gtg tgc aag aag tgc ccg cca cag cgc ctg gcg cgt ttc gag gag gag<br>Val Cys Lys Lys Cys Pro Pro Gln Arg Leu Ala Arg Phe Glu Glu Glu<br>        235                 240                 245 | 1133 |
| tgc cgc aag tac cgc aca cta gtc ata aag ggt gtg cgc gtc ttc gac<br>Cys Arg Lys Tyr Arg Thr Leu Val Ile Lys Gly Val Arg Val Phe Asp<br>    250                 255                 260 | 1181 |
| gtg gcg gtc ttg gcg cca ctg ctg cga gac ccg gcc ctg gac ctc aag<br>Val Ala Val Leu Ala Pro Leu Leu Arg Asp Pro Ala Leu Asp Leu Lys<br>265                 270                 275                 280 | 1229 |
| gtc atc cac ttg gtg cgt gat ccc cgc gcg gtg gcg agt tca cgg atc<br>Val Ile His Leu Val Arg Asp Pro Arg Ala Val Ala Ser Ser Arg Ile<br>                285                 290                 295 | 1277 |
| cgc tcg cgc cac ggc ctc atc cgt gag agc cta cag gtg gtg cgc agc<br>Arg Ser Arg His Gly Leu Ile Arg Glu Ser Leu Gln Val Val Arg Ser<br>            300                 305                 310 | 1325 |

-continued

| | |
|---|---|
| cga gac ccg cga gct cac cgc atg ccc ttc ttg gag gcc gcg ggc cac<br>Arg Asp Pro Arg Ala His Arg Met Pro Phe Leu Glu Ala Ala Gly His<br>315                    320                    325 | 1373 |
| aag ctt ggc gcc aag aag gag ggc gtg ggc ggc ccc gca gac tac cac<br>Lys Leu Gly Ala Lys Lys Glu Gly Val Gly Gly Pro Ala Asp Tyr His<br>330                    335                    340 | 1421 |
| gct ctg ggc gct atg gag gtc atc tgc aat agt atg gct aag acg ctg<br>Ala Leu Gly Ala Met Glu Val Ile Cys Asn Ser Met Ala Lys Thr Leu<br>345                    350                    355                    360 | 1469 |
| cag aca gcc ctg cag ccc cct gac tgg ctg cag ggc cac tac ctg gtg<br>Gln Thr Ala Leu Gln Pro Pro Asp Trp Leu Gln Gly His Tyr Leu Val<br>                    365                    370                    375 | 1517 |
| gtg cgg tac gag gac ctg gtg gga gac ccc gtc aag aca cta cgg aga<br>Val Arg Tyr Glu Asp Leu Val Gly Asp Pro Val Lys Thr Leu Arg Arg<br>380                    385                    390 | 1565 |
| gtg tac gat ttt gtg gga ctg ttg gtg agc ccc gaa atg gag cag ttt<br>Val Tyr Asp Phe Val Gly Leu Leu Val Ser Pro Glu Met Glu Gln Phe<br>                    395                    400                    405 | 1613 |
| gcc ctg aac atg acc agt ggc tcg ggc tcc tcc tcc aag cct ttc gtg<br>Ala Leu Asn Met Thr Ser Gly Ser Gly Ser Ser Ser Lys Pro Phe Val<br>410                      415                    420 | 1661 |
| gta tct gca cgc aat gcc acg cag gcc gcc aat gcc tgg cgg acc gcc<br>Val Ser Ala Arg Asn Ala Thr Gln Ala Ala Asn Ala Trp Arg Thr Ala<br>425                    430                    435                    440 | 1709 |
| ctc acc ttc cag cag atc aaa cag gtg gag gag ttt tgc tac cag ccc<br>Leu Thr Phe Gln Gln Ile Lys Gln Val Glu Glu Phe Cys Tyr Gln Pro<br>                    445                    450                    455 | 1757 |
| atg gcc gtc ctg ggc tat gag cgg gtc aac agc cct gag gag gtc aaa<br>Met Ala Val Leu Gly Tyr Glu Arg Val Asn Ser Pro Glu Glu Val Lys<br>460                      465                    470 | 1805 |
| gac ctc agc aag acc ctg ctt cgg aag ccc cgt ctc taaaagggt<br>Asp Leu Ser Lys Thr Leu Leu Arg Lys Pro Arg Leu<br>475                    480 | 1851 |
| tcccaggaga cctgattccc tgtggtgata cctataaaga ggatcgtagt gtgtttaaat | 1911 |
| aaacacagtc cagactcaaa cggaggaagc ccacatattc tattatagat atataaataa | 1971 |
| tcacacacac acttgctgtc aatgttttga gtcagtgcat ttcaaggaac agccacaaaa | 2031 |
| tacacacccc taagaaaagg caagacttga acgttctgac caggtgcccc tcttcttctt | 2091 |
| tgccttctct tgtcctcttt ctcctatttc ttaccctgtc ctccacctgc cttccatttt | 2151 |
| gaagtgggat gttaatgaaa tcaagttcca gtaacccaaa tcttgtttac aaaatattcg | 2211 |
| tggtatctgt gaacatgtta agagtaattt ggatgtgggg gtggggtgg agaaagggga | 2271 |
| agtggtccag aaacaaaaag ccccattggg catgataagc cgaggaggca ttcttcctaa | 2331 |
| aagtagactt ttgtgtaaaa agcaaaggtt acatgtgagt attaataaag aagataataa | 2391 |
| ataaaaaaaa aaaaaaaa | 2409 |

<210> SEQ ID NO 4
<211> LENGTH: 484
<212> TYPE: PRT
<213> ORGANISM: Homo sapiens

<400> SEQUENCE: 4

Met Lys Val Phe Arg Arg Lys Ala Leu Val Leu Cys Ala Gly Tyr Ala
1               5                    10                    15

Leu Leu Leu Val Leu Thr Met Leu Asn Leu Leu Asp Tyr Lys Trp His
               20                    25                    30

```
Lys Glu Pro Leu Gln Gln Cys Asn Pro Asp Gly Pro Leu Gly Ala Ala
         35                  40                  45

Ala Gly Ala Ala Gly Gly Lys Leu Gly Ala Pro Arg Ala Ala Ser Gly
 50                  55                  60

Arg Ala Ala Pro Cys Ser Cys Pro Phe Gly Pro Pro His Ser Leu Pro
 65                  70                  75                  80

Pro Ser Arg Cys Arg Arg Arg Gly Asp Thr Leu Gln Pro Arg Gln Gly
                 85                  90                  95

Trp Arg Gly Leu Arg Pro Leu Gln Ala Met Ala Leu Gly Ala Pro Glu
                100                 105                 110

Gly Val Gly Asp Lys Arg His Trp Met Tyr Val Phe Thr Thr Trp Arg
            115                 120                 125

Ser Gly Ser Ser Phe Phe Gly Glu Leu Phe Asn Gln Asn Pro Glu Val
        130                 135                 140

Phe Phe Leu Tyr Glu Pro Val Trp His Val Trp Gln Lys Leu Tyr Pro
145                 150                 155                 160

Gly Asp Ala Val Ser Leu Gln Gly Ala Ala Arg Asp Met Leu Ser Ala
                165                 170                 175

Leu Tyr Arg Cys Asp Leu Ser Val Phe Gln Leu Tyr Ser Pro Ala Gly
                180                 185                 190

Ser Gly Gly Arg Asn Leu Thr Thr Leu Gly Ile Phe Gly Ala Ala Thr
        195                 200                 205

Asn Lys Val Val Cys Ser Ser Pro Leu Cys Pro Ala Tyr Arg Lys Glu
        210                 215                 220

Val Val Gly Leu Val Asp Asp Arg Val Cys Lys Lys Cys Pro Pro Gln
225                 230                 235                 240

Arg Leu Ala Arg Phe Glu Glu Cys Arg Lys Tyr Arg Thr Leu Val
                245                 250                 255

Ile Lys Gly Val Arg Val Phe Asp Val Ala Val Leu Ala Pro Leu Leu
                260                 265                 270

Arg Asp Pro Ala Leu Asp Leu Lys Val Ile His Leu Val Arg Asp Pro
        275                 280                 285

Arg Ala Val Ala Ser Ser Arg Ile Arg Ser Arg His Gly Leu Ile Arg
    290                 295                 300

Glu Ser Leu Gln Val Val Arg Ser Arg Asp Pro Arg Ala His Arg Met
305                 310                 315                 320

Pro Phe Leu Glu Ala Ala Gly His Lys Leu Gly Ala Lys Lys Glu Gly
                325                 330                 335

Val Gly Gly Pro Ala Asp Tyr His Ala Leu Gly Ala Met Glu Val Ile
            340                 345                 350

Cys Asn Ser Met Ala Lys Thr Leu Gln Thr Ala Leu Gln Pro Pro Asp
        355                 360                 365

Trp Leu Gln Gly His Tyr Leu Val Val Arg Tyr Glu Asp Leu Val Gly
    370                 375                 380

Asp Pro Val Lys Thr Leu Arg Arg Val Tyr Asp Phe Val Gly Leu Leu
385                 390                 395                 400

Val Ser Pro Glu Met Glu Gln Phe Ala Leu Asn Met Thr Ser Gly Ser
                405                 410                 415

Gly Ser Ser Ser Lys Pro Phe Val Val Ser Ala Arg Asn Ala Thr Gln
            420                 425                 430

Ala Ala Asn Ala Trp Arg Thr Ala Leu Thr Phe Gln Gln Ile Lys Gln
        435                 440                 445

Val Glu Glu Phe Cys Tyr Gln Pro Met Ala Val Leu Gly Tyr Glu Arg
```

```
                 450                 455                 460
Val Asn Ser Pro Glu Glu Val Lys Asp Leu Ser Lys Thr Leu Leu Arg
465                 470                 475                 480

Lys Pro Arg Leu

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
gtcgtcggac tggtggacga                                          20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
cccagagcgt ggtagtctgc                                          20

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
acgaattcgg gatgaaggta tttcgcagg                                29

<210> SEQ ID NO 8
<211> LENGTH: 29
<212> TYPE: DNA
<213> ORGANISM: Artificial Sequence
<220> FEATURE:
<223> OTHER INFORMATION: primer

<400> SEQUENCE: 8
atgaattctc aaagccgggg cttcctgag                                29

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
ctgaattcgg aatgaaggtg ttccgta                                  27

<210> SEQ ID NO 10
<211> LENGTH: 27
<212> TYPE: DNA
<213> ORGANISM: Artificial Sequence
<220> FEATURE:
<223> OTHER INFORMATION: primer

<400> SEQUENCE: 10
gagaattctt agagacgggg cttccga                                  27
```

POLYPEPTIDE OF N-ACETYLGLUCOSAMINE-6-O-SULFOTRANSFERASE AND DNA ENCODING THE SAME

FIELD OF THE INVENTION

The present invention relates to a polypeptide of N-acetylglucosamine-6-O-sulfotransferase and a DNA having a nucleotide sequence encoding the polypeptide.

DESCRIPTION OF THE PRIOR ART

The closest prior art is described below.

It has been described in Biochem. J., 319, 209–216 (1996) and J. Biol. Chem. 272, 29493–29501 (1997) that rat and human microsome fractions had an N-acetylglucosamine-6-O-sulfotransferase activity. However, there has been so far no report about isolation and identification of a polypeptide of N-acetylglucosamine-6-O-sulfotransferase. A DNA encoding this polypeptide has not also been known.

Once a polypeptide of N-acetylglucosamine-6-O-sulfotransferase is obtained, it can be used for synthesis of sugar chains such as GlyCAM-1 that is a ligand of L-selectin (which is involved in homing of lymphocytes and rolling of leukocytes occurring at the early stage of inflammation). A DNA encoding this polypeptide would be expected to be used for large scale production of the polypeptide, or artificial synthesis of GlyCAM-1 (having a structure of NeuAcα2-3Galβ1-4(Fucα1-3) (SO$_4$-6)GlcNAc-) by using transformants which harbors the DNA.

SUMMARY OF THE INVENTION

An object of the present invention is to provide a polypeptide of N-acetylglucosamine-6-O-sulfotransferase and a DNA encoding the polypeptide.

The present inventors have succeeded in cloning a DNA encoding a polypeptide of N-acetylglucosamine-6-O-sulfotransferase, having an activity to specifically transfer a sulfate group to a hydroxyl group at 6 position of an N-acetylglucosamine residue located at a non-reducing end of GlcNAcβ1-3Galβ1-4GlcNAc, wherein GlcNAc represents an N-acetylglucosamine residue, Gal represents a galactose residue, β1-3 represents a β1-3 glycosidic linkage, and β1-4 represents a β1-4 glycosidic linkage. The inventors have also confirmed that the polypeptide of N-acetylglucosamine-6-O-sulfotransferase was expressed by the DNA and identified the polypeptide, thereby completing the present invention.

The present invention provides a polypeptide of (a) or (b) below (hereinafter sometimes referred to as "the polypeptide of the present invention"):

(a) a polypeptide consisting of an amino acid sequence represented by SEQ ID NO: 2; or (b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

wherein GlcNAc represents an N-acetylglucosamine residue, Gal represents a galactose residue, β1-3 represents a β1-3 glycosidic linkage, and β1-4 represents a β1-4 glycosidic linkage.

The polypeptide of the present invention also includes a polypeptide of (a) or (b) below:

(a) a polypeptide consisting of the amino acid sequence represented by SEQ ID NO: 4; or (b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

wherein GlcNAc represents an N-acetylglucosamine residue, Gal represents a galactose residue, β1-3 represents a β1-3 glycosidic linkage, and β1-4 represents a β1-4 glycosidic linkage.

The polypeptide of the present invention also includes a polypeptide having the following properties:

(1) Action: a sulfate group is transferred from a sulfate group donor to a hydroxyl group at 6 position of an N-acetylglucosamine residue located at a non-reducing end of an oligosaccharide represented by the formula I:

wherein GlcNAc represents an N-acetylglucosamine residue, Gal represents a galactose residue, β1-3 represents a β1-3 glycosidic linkage, and β1-4 represents a β1-4 glycosidic linkage;

(2) Substrate specificity: sulfate group is not transferred to chondroitin, chondroitin 4-sulfate, chondroitin 6-sulfate, dermatan sulfate, keratan sulfate, desulfated keratan sulfate, CDSNS-heparin, mucin from porcine stomach, mucin from bovine submaxillary gland, and an oligosaccharide represented by the formula II:

wherein GlcNAc represents an N-acetylglucosamine residue, Gal represents a galactose residue, β1-3 represents a β1-3 glycosidic linkage, and β1-4 represents a β1-4 glycosidic linkage; and (3) N-terminal amino acid sequence comprises an amino acid sequence represented by amino acid numbers 1 to 48 in SEQ ID NO: 2.

The present invention provides a DNA encoding a polypeptide of (a) or (b) below (hereinafter sometimes referred to as "the DNA of the present invention"):

(a) a polypeptide consisting of an amino acid sequence represented by SEQ ID NO: 2; or (b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

wherein GlcNAc represents an N-acetylglucosamine residue, Gal represents a galactose residue, β1-3 represents a β1-3 glycosidic linkage, and β1-4 represents a β1-4 glycosidic linkage.

The DNA of the present invention also includes a DNA encoding a polypeptide of (a) or (b) below:

(a) a polypeptide consisting of an amino acid sequence represented by SEQ ID NO: 4; or
(b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

GlcNAcβ1-3Galβ1-4GlcNAc  (I)

wherein GlcNAc represents an N-acetylglucosamine residue, Gal represents a galactose residue, β1-3 represents a β1-3 glycosidic linkage, and β1-4 represents a β1-4 glycosidic linkage.

The DNA of the present invention is preferably a DNA comprising a nucleotide sequence represented by nucleotide numbers 470 to 1918 in SEQ ID NO: 1 and a DNA comprising a nucleotide sequence represented by nucleotide numbers 390 to 1841 in SEQ ID NO: 3.

The present invention also provides a method of producing a sulfated sugar (hereinafter sometimes referred to as "the producing method 1 of the present invention") represented by the formula III:

(SO$_4$-6)GlcNAc—R  (III)

wherein GlcNAc represents an N-acetylglucosamine residue; SO$_4$-6 means that a hydroxyl group at 6 position is sulfated, and —R represents a hydrogen atom or a sugar residue bonded by a glycosidic linkage, which comprises a step of reacting the above-described polypeptide with a sugar chain represented by the formula IV:

GlcNAc—R  (IV)

wherein GlcNAc represents an N-acetylglucosamine residue, and —R represents a hydrogen atom or a sugar residue bonded by a glycosidic linkage.

Furthermore, the present invention provides a method of producing a sulfated sugar (hereinafter sometimes referred to as "the producing method 2 of the present invention"), which comprises a step of transfecting a cell with the DNA of the present invention into and then culturing the cell. A preferred embodiment of this method is a method of transfecting a cell with the DNA of the present invention and a cDNA encoding fucosyltransferase concurrently.

The present invention further provides an antibody that reacts with 6-sulfated sialyl Lewis X but does not react with 6'-sulfated sialyl Lewis X, 6,6'-bis-sulfated sialyl Lewis X, 6-sulfated Lewis X and Lewis X.

The present invention still further provides an antibody that specifically reacts with a sugar chain represented by the following formula:

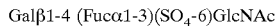

Galβ1-4 (Fucα1-3)(SO$_4$-6)GlcNAc

The present invention also provides an antibody that reacts with a sugar chain represented by the following formula:

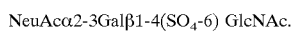

NeuAcα2-3Galβ1-4(SO$_4$-6) GlcNAc.

A:GlcNAcβ1-3Galβ1-4GlcNAc as the sulfate group acceptor.

B: Galβ1-4GlcNAcβ1-3Galβ1-4GlcNAc (L1L1) as the sulfate group acceptor. After the enzyme reaction, the products were analyzed by Superdex 30 Gel chromatography. "●" indicates in the presence of acceptors; "○" indicates in the absence of acceptors. Arrows indicates the elution position of acceptors.

Figure 3:
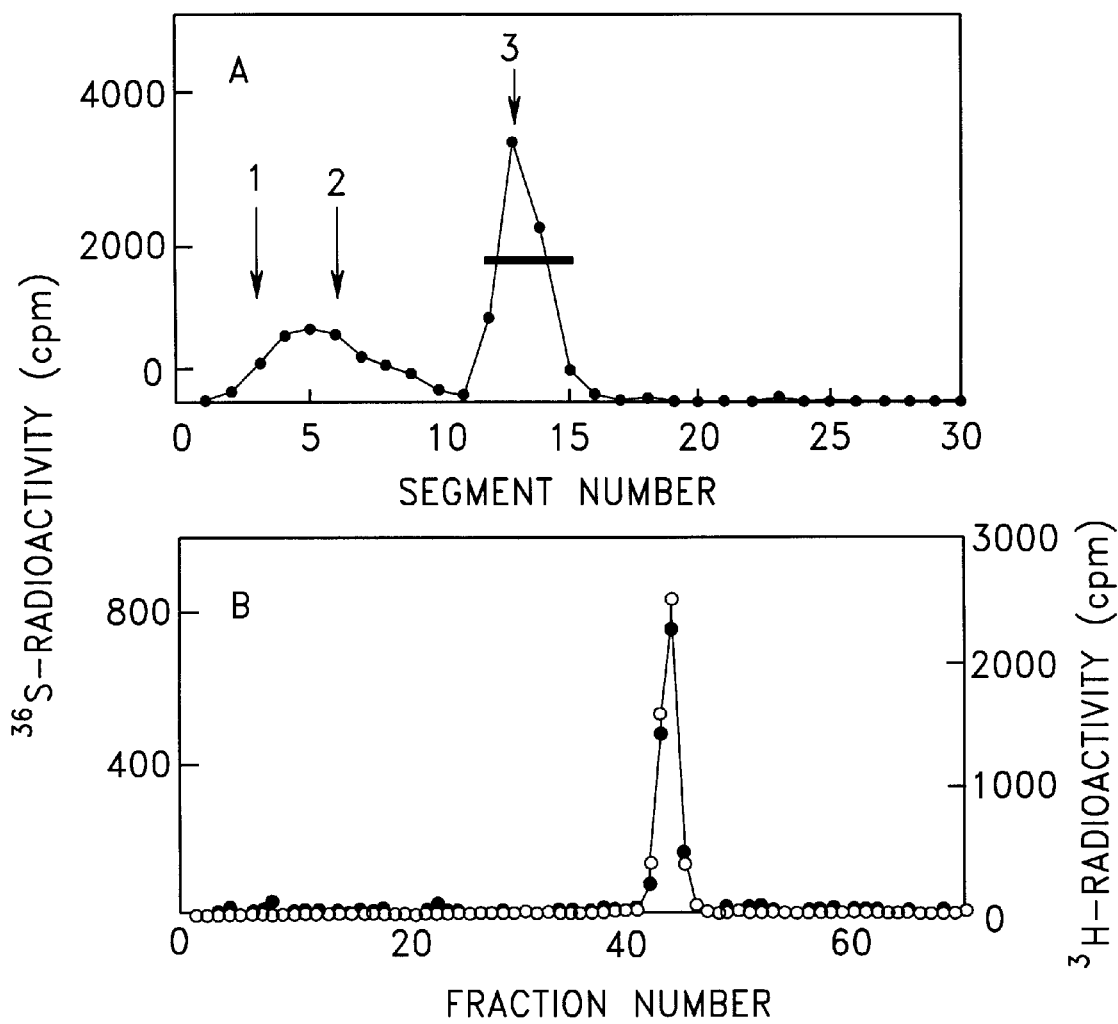

FIGS. 3A and B. shows the assay result of sulfated products with the polypeptide of the present invention derived from mouse.

A: $^{35}$S-Labeled GlcNAcβ1-3Galβ1-4GlcNAc was N-deacetylated, deamino-cleaved and reduced and separated by paper chromatography. Arrows 1,2, and 3 indicate the migration position of standard substances: 1, (SO$_4$-6)Galβ1-4(SO$_4$-6)2,5-anhydromannitol; 2, Galβ1-4(SO$_4$-6)2,5-anhydromannitol; 3, (SO$_4$-6)2,5-anhydromannitol.

B: $^{35}$S Labeled (SO$_4$-6)2,5-anhydromannitol fraction, which was shown by a horizontal bar in A) was mixed with $^3$H-labeled (SO$_4$-6)2,5-anhydromannitol (standard) and analyzed by HPLC using a SAX-10 column. Radioactivity of $^3$H (○) and $^{35}$S (●) of each fracton was determined.

Figure 4:
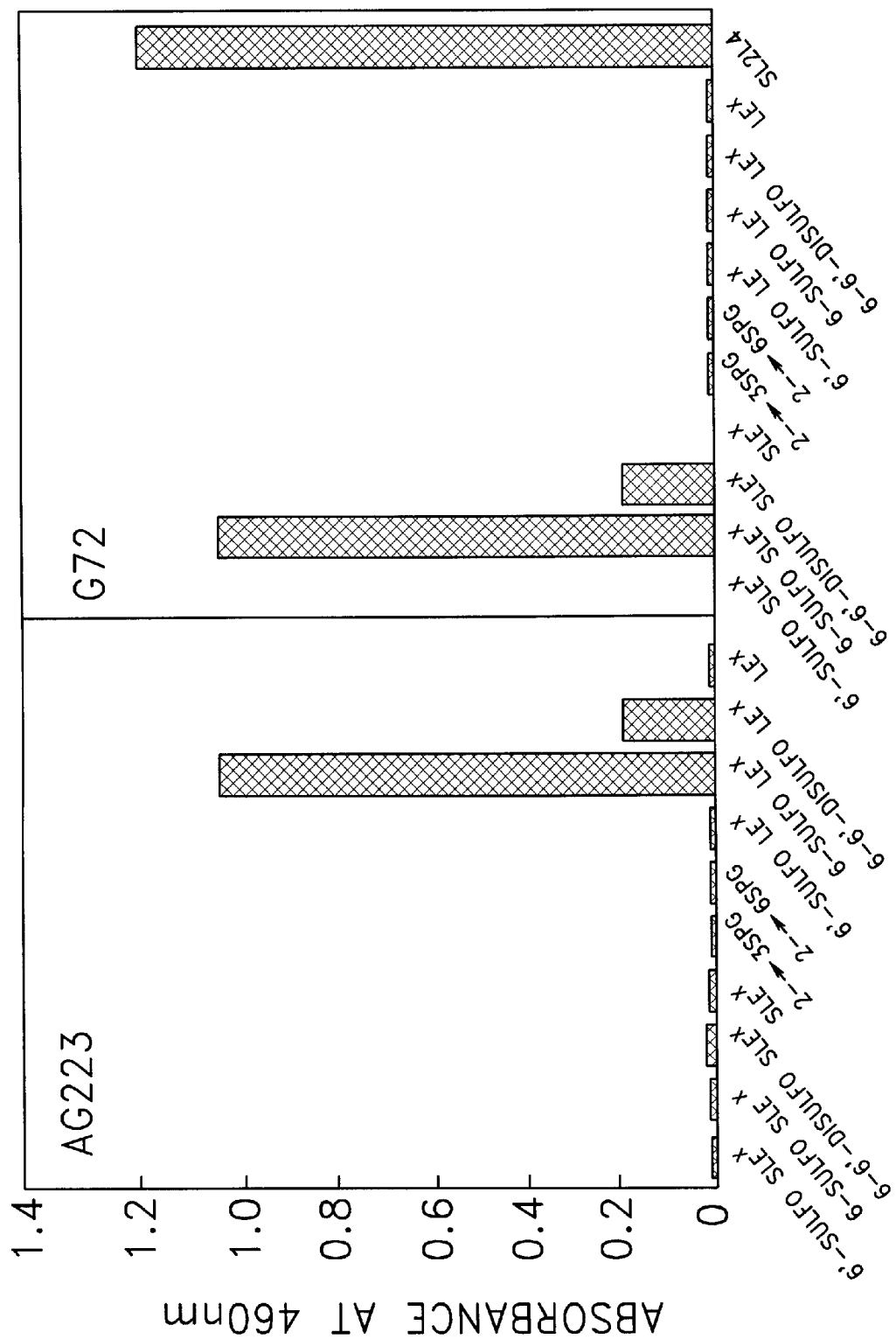

FIG. 4 shows the assay result of the specificity of AG223 and G72 monoclonal antibodies by ELISA. Glycolipids were immobilized at the bottom of 96-well culture plates and ELISA assays were performed. "S" indicates NeuAc, "Lex" indicates Lewis X ceramide, "PG" indicates paragloboside, "SL2L4" indicates NeuAcα2-3Galβ1-4(SO$_4$-6)GlcNAcβ1-3(SO$_4$-6)Galβ1-4(SO$_4$-6)GlcNAc-chol esteryl aniline, respectively.

Figure 5:
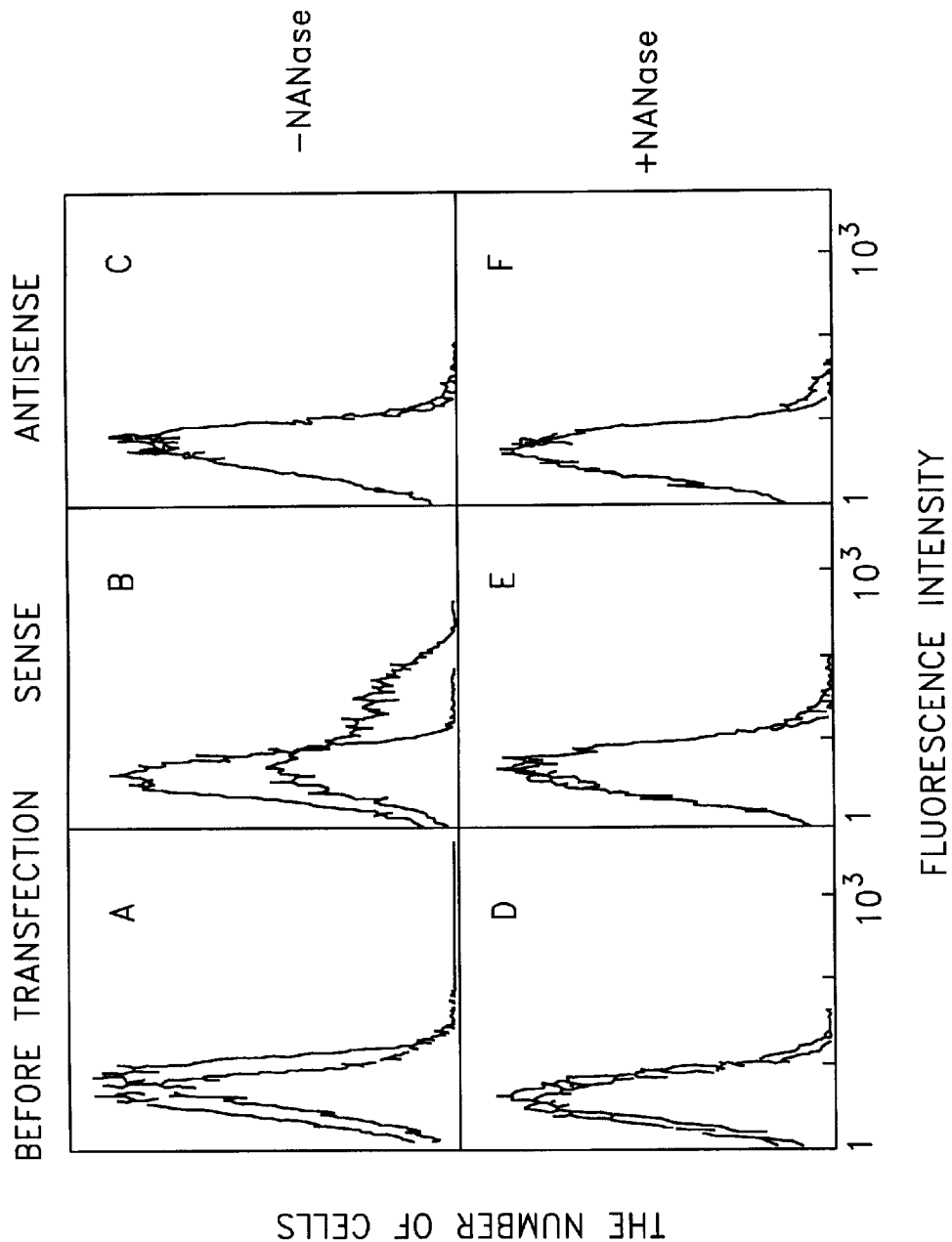

FIGS. 5A, B, C, D, E, and F. shows the expression of G72 antigen by transfection with the DNA of the present invention derived from mouse.

COS-7 cells before transfection(A, D), or the cells transfected with the sense (the correct orientation) cDNA (B, E) or with the antisense (the reverse orientation) cDNA (C, F) were reacted with C72 monoclonal antibody and analyzed by FACS. Thick lines are the pattern after reaction with the antibody, and thin lines are those before the reaction. "–NANase" indicates a result before neuraminidase digestion, "+NANase" indicates a result after digestion with 0.02 units/ml of Arthrobacter ureafaciens neuraminidase in PBS, (pH 7.4) at 37° C. for 30 min.

Figure 6:
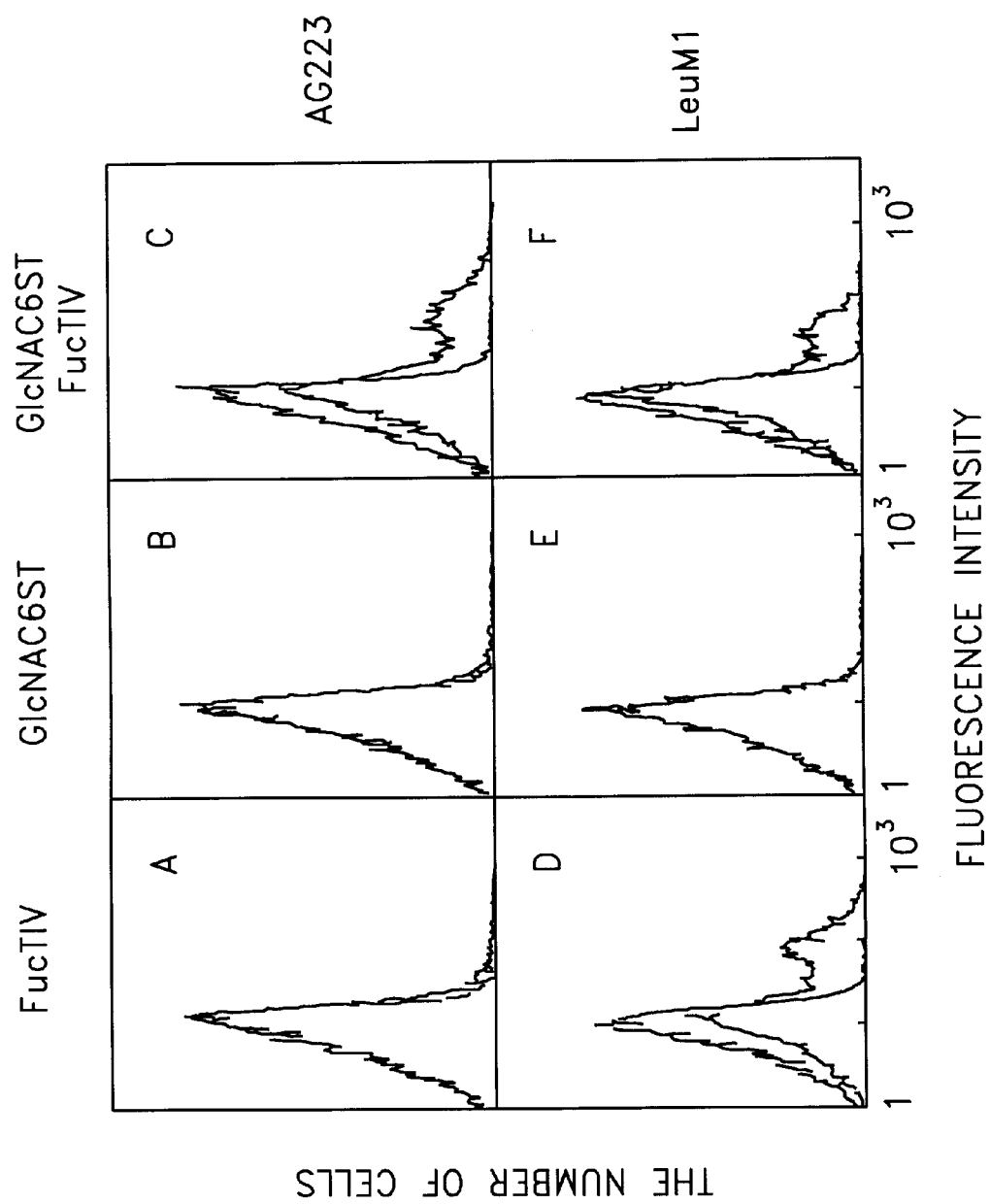

FIGS. 6A, B, C, D, E, and F shows the expression of AG223 (6-sulfo Lewis X) antigen by double transfection with the DNA of the present invention derived from mouse and fucosyltransferase IV cDNA. COS-7 cells transfected with the fucosyltransferase cDNA alone (A, D), the DNA of the present invention alone (B, E) or both the DNA (C, F) were reacted with AG223 monoclonal antibody (A-C) or with LeuM1 (anti-Lewis X antibody) (D-F), and analyzed by FACS. Thick lines are the pattern after reaction with antibody, and thin lines are those before the reaction.

Figure 7:
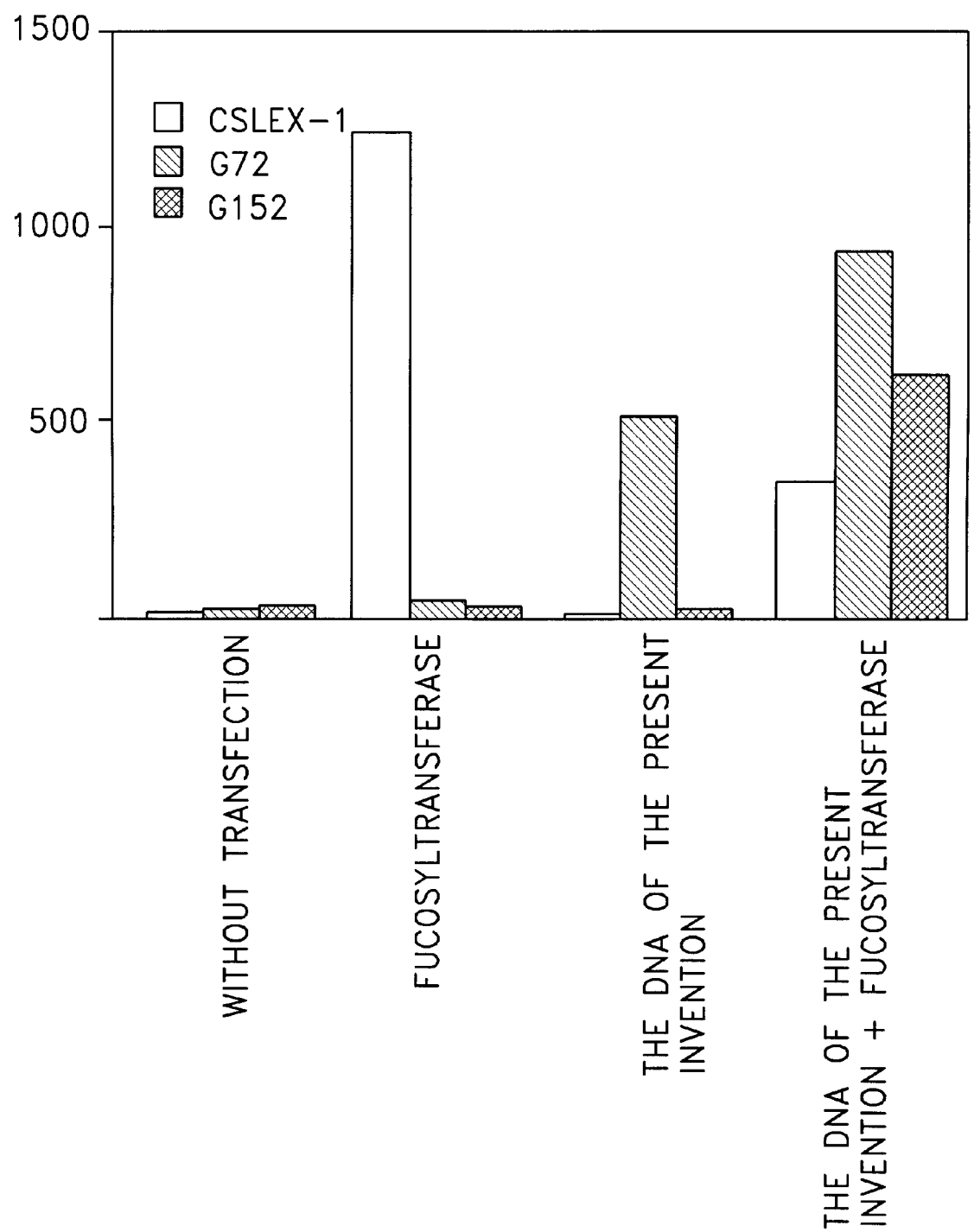

FIG. 7 shows the expression of G72 antigen (6-sulfo sialyl N-acetyllactosamine antigen) by transfection with the DNA of the present invention derived from human, and the expression of G152 antigen (6-sulfosialyl Lewis X antigen)

by double transfection with the DNA of the present invention derived from human and fucosyltransferase IV cDNA.

A data shows mean fluorescence intensity of antigen positive group in transfected cells.

Figure 8:
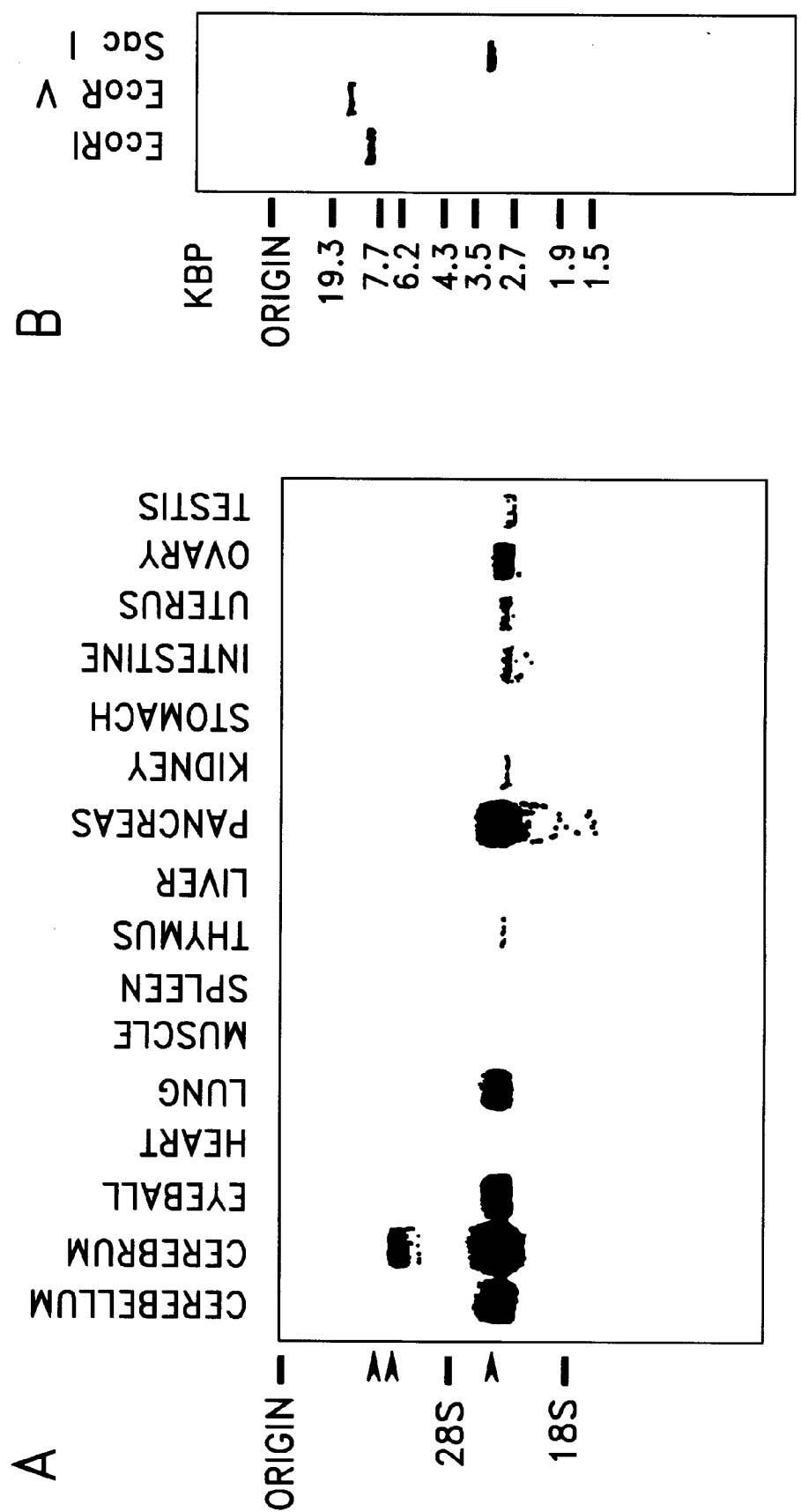

FIGS. 8A and B. shows the result of Northern and Southern analyses of the DNA of the present invention derived from mouse.

A: Nothern blot analysis. Arrowheads indicate the positions of different mRNAs of 13.5, 9.8, and 3.9 kb. The positions of ribosomal RNAs are indicated at the left. Hybridization with a glyceroaldehyde 3-phosphate dehydrogenase probe revealed similar intensity of bands in each lane, except that in the pancreas the intensity was weak. B: Genomic Southern blot analysis. Single bands were detected after digestion with EcoRI, EcoRV or SacI.

DETAILED DESCRIPTION OF THE INVENTION

The mode for carrying out the present invention is described below.

Unless otherwise specified herein, Gal represents a galactose residue, GlcNAc represents an N-acetylglucosamine residue, NeuAc represents an N-acetylneuraminic acid residue, Fuc represents a fucose residue, β1-3 represents a β1-3 glycosidic linkage, β1-4 represents a β1-4 glycosidic linkage, α2-3 represents a α2-3 glycosidic linkage, α1-3 represents a α1-3 glycosidic linkage, $SO_4$-6 represents that a hydroxyl group at 6 position is sulfated, and Cer represents a ceramide residue, respectively.

<1> The Polypeptides of the Present Invention

The polypeptide of the present invention is a polypeptide of (a) or (b) below:

(a) a polypeptide consisting of an amino acid sequence represented by SEQ ID NO: 2; or (b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

GlcNAcβ1-3Galβ1-4GlcNAc          (I)

The polypeptide (a) is preferred among them.

In this specification, the term "a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I (GlcNAcβ1-3Galβ1-4GlcNAc)" means that one or more amino acid residues of the polypeptide may be substituted, deleted, inserted, or transferred as long as such modification does not substantially affect the activity to selectively transfer a sulfate group from a sulfate group donor to a hydroxyl group at 6 position of an N-acetylglucosamine residue located at a non-reducing end of GlcNAcβ1-3Galβ1-4GlcNAc.

Mutation such as substitution, deletion, insertion, or transposition of amino acid residues may occur in the amino acid sequence of the polypeptides existing in nature due to, for example, the modifying reaction of the biosynthesized polypeptides in the living oraganisms or during their purification as well as polymorphism and mutation of the DNAs encoding the polypeptides, nevertheless some of mutated polypeptides are known to have substantially the same physiological and biological activities as the intact polypeptides that have not been mutated. The polypeptide of the present invention includes those having slightly different structures but not having a significant difference in the functions. The polypeptide of the present invention also includes those which have been artificially treated to have mutation as described above in the amino acid sequences. In this case, a further variety of mutants can be produced. For example, a polypeptide having a human interleukin 2 (IL-2) amino acid sequence, in which a cysteine residue has been replaced with a serine residue, is known to retain the interleukin 2 activities (Science 224, 1431 (1984)). Furthermore, a polypeptide of certain kind is known to have a pepctide region that is not essential for exhibiting its activities. Examples of such polypeptides include a signal peptide contained in a polypeptide that is secreted extracellularly and a pro-sequence found in a precursor of protease, and the like. Most of these regions are removed after translation or upon conversion into an active form of the polypeptides. These polypeptides exist in different primary structures but finally have equivalent functions. Such polypeptides are also included in the polypeptide of the present invention.

The term "few amino acids" used herein means the number of amino acid residues that may be mutated to the extent that the activities of the polypeptide of the present invention are not lost. For example, in a polypeptide consisting of 400 amino acid residues, about 20 or less of amino acid residues may be mutated.

The enzymatic activity to transfer a sulfate group from a sulfate group donor to a hydroxyl group at 6 position of an N-acetylglucosamine residue located at a non-reducing end of an oligosaccharide represented by GlcNAcβ1-3Galβ1-4GlcNAc can be determined by the method of measuring the activities of the polypeptide of the present invention as will be described later. Determining whether the presence or absence of the activities of the polypeptide of the present invention as an index, one of ordinary skilled in the art would readily select substitution, deletion, insertion, or transposition of one or more amino acid residues, which does not substantially affect the activities of the polypeptide.

This polypeptide has been obtained from a mouse originally. As a matter of course, however, the polypeptide of the present invention also includes polypeptides produced by genetic engineering procedure or chemical synthesis.

The polypeptide of the present invention also includes a polypeptide of (a) or (b) below:

(a) a polypeptide consisting of an amino acid sequence represented by SEQ ID NO: 4; or (b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

GlcNAcβ1-3Galβ3-4GlcNAc          (I)

Among the above polypeptides, the polypeptide (a) (the polypeptide consisting of an amino acid sequence represented by SEQ ID NO: 4) is preferred because it has 85% or more homology to the above-described polypeptide (a) of the present invention (the polypeptide consisting of an amino acid sequence represented by SEQ ID NO: 2).

Thus, the polypeptide of the present invention includes polypeptides having 85% or more homology to the polypeptide consisting of the amino acid sequence represented by SEQ ID NO: 2).

This polypeptide has been derived from human originally. As a matter of course, however, the polypeptide of the present invention also includes polypeptides produced by genetic engineering procedure or chemical synthesis.

The polypeptide of the present invention also includes a polypeptide having the Following properties:

(1) Action

It transfers a sulfate group from a sulfate group donor to a hydroxyl group at 6 position of an N-acetylglucosamine residue located at a non-reducing end of an oligosaccharide represented by the formula I:

GlcNAcβ1-3Galβ1-4GlcNAc (I);

(2) Substrate Specificity

It does not transfer a sulfate group to chondroitin, chondroitin 4-sulfate, chondroitin 6-sulfate, dermatan sulfate, keratan sulfate, desulfated keratan sulfate, CDSNS-heparin, mucin From porcine stomach, mucin from bovine submaxillary gland, and an oligosaccharide represented by the formula II:

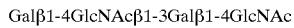

Galβ1-4GlcNAcβ1-3Galβ1-4GlcNAc (II);

and (3) N-terminal Amino Acid Sequence

It consists of an amino acid sequence represented by amino acid numbers 1 to 48 in SEQ ID NO: 2.

For the polypeptide of the present Invention, 3'-phosphoadenosine 5'-phosphosulfate (hereinafter sometimes referred to as "PAPS") is preferably used as a sulfate group donor.

These polypeptides of the present invention can be produced by isolation and purification from natural source or by chemical synthesis since their amino acid sequences and properties are disclosed by this invention. Preferably, the polypeptide is produced using the DNA of the present invention as will be described later. The method of producing the polypeptide of the present invention using the DNA of the present invention will be described later. The polypeptide of the present invention is not necessarily a single polypeptide but may be a part of a fusion protein if necessary. For example, a fusion protein comprising the polypeptide of the present invention and another polypeptide necessary for expression may be exemplified.

Since the polypeptide of the present invention has an activity to specifically transfer a sulfate group from a sulfate group donor to a hydroxyl group at 6 position of an N-acetylglucosamine residue located at a non-reducing end of GlcNAcβ1-3Galβ1-4GlcNAc, the polypeptide of the present invention can be used for specifically sulfating the 6 position of an N-acetylglucosamine residue located at a non-reducing end, synthesizing sugar chains having a GlyCAM-1 structure and so on.

<2> The DNA of the Present Invention

The DNA of the present invention is a DNA encoding a polypeptide of (a) or (b) below:

(a) a polypeptide consisting of an amino acid sequence represented by SEQ ID NO: 2; or (b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

GlcNAcβ1-3Galβ1-4GlcNAc (I).

Among these, a DNA encoding the polypeptide (a) is preferable.

For example of such DNA, a DNA containing a nucleotide sequence represented by nucleotide numbers 470 to 1918 in SEQ ID NO: 1, may be exemplified.

Furthermore this DNA has been derived from mouse originally. As a matter of course, however, the source of the DNA of the present invention is not limited and the DNA also includes that is produced by genetic engineering procedure or chemical synthesis.

The DNA of the present invention also includes a DNA encoding a polypeptide of (a) or (b) below:

(a) a polypeptide consisting of an amino acid sequence represented by SEQ ID NO: 4; or (b) a polypeptide which comprises an amino acid sequence including substitution, deletion, insertion or transposition of one or few amino acids in the amino acid sequence of (a) and which has an enzymatic activity to transfer a sulfate group from a sulfate group donor to a hydroxyl group at 6 position of an N-acetylglucosamine residue located at a non-reducing end of an oligosaccharide represented by the formula I:

GlcNAcβ1-3Galβ1-4GlcNAc (I).

Among these, the DNA encoding the polypeptide (a) is preferred because the polypeptide of the present invention encoded by the DNA has 85% or more homology to the polypeptide of the present invention consisting of an amino acid sequence represented by SEQ ID NO: 2.

As a specific example of such DNA, for example a DNA comprising the nucleotide sequence represented by nucleotide numbers 390 to 1841 in SEQ ID NO: 3, may be exemplified.

Furthermore this DNA has been derived from human originally. As a matter of course, however, the source of the DNA of the present invention is not limited and the DNA also includes that is produced by genetic engineering procedure or chemical synthesis.

Furthermore one of ordinary skilled in the art would readily understand that the DNA of the present invention includes DNA having the nucleotide sequence different from that as described above due to degeneracy of the genetic codes.

The DNA of the present invention also includes DNA or RNA complementary to the DNA of the present invention. Furthermore, the DNA of the present invention may be either a single-stranded coding chain encoding the polypeptide of the present invention or a double-stranded chain consisting of the above single-stranded chain and a DNA or a RNA having complementary nucleotide sequence thereto.

As described in <1> above, the polypeptide of the present invention includes polypeptides which are slightly different in structure but are not significantly different in function from the polypeptide of the present invention. The DNA of the present invention also includes DNA encoding polypeptides which are slightly different in structure but are not significantly different in function from the polypeptide of the present invention.

A specific example of such DNA is a DNA which is slightly different in structure from the DNA of the present invention due to polymorphism or mutation of DNA but which encodes a polypeptide having the function substantially equivalent to that of the polypeptide of the present invention.

The gene encoding the polypeptide of the present invention derived from a chromosome is expected to contain introns in the coding region. DNA fragments separated by introns are also included in the DNA of the present invention as long as the fragments encodes the polypeptide of the present invention. Namely the meaning of the term "encode" used herein covers to have a nucleotide sequence that undergoes processing upon transcription and finally becomes capable of expressing a desired polypeptide.

For the DNA of the present invention, PAPS is preferred as a sulfate group donor.

1. The Method of Producing the DNA of the Present Invention

Since the nucleotide sequence of the DNA of the present invention was revealed by the present invention, the DNA can be synthesized based on the sequence. Alternatively, the DNA can be obtained by amplifying the DNA of the present invention from a chromosomal DNA or mRNA by polymerase chain reaction method (PCR) using oligonucleotide primers prepared based on the sequence. The DNA of the present invention was obtained for the first time by the cDNA cloning comprising the following steps as described in the examples below.

(1) Production of the DNA of the Present Invention Derived from Mouse:
  i) preparation of oligonucleotide primers for PCR;
  ii) amplification by reverse transcription PCR (RT-PCR) using a mouse total RNA;
  iii) screening the DNA of the present invention from a mouse cDNA library using the PCR products.

(2) Production of the DNA of the Present Invention Derived from Human:
  i) screening the DNA of the present invention from a human cDNA library using the cDNA obtained in iii) of (1) above;
  ii) Sequencing nucleotide sequence of the cDNA thus obtained.

But the method of producing the DNA of the present invention is not to be limited to the above method. The DNA of the present invention can be prepared by other known cDNA cloning methods.

An example of the method of producing the DNA of the present invention is described in detail below.

(1) Preparation of Oligonucleotide Primers for PCR

Oligonucleotide primers (a sense primer and an antisense primer) are prepared based on a mouse expressed sequence tag (EST) sequence (Genbank accession number, AA103962) having homology to the catalytic site of mouse chondroitin 6-sulfotransferase. Specific examples as oligonucleotide primers are 5'-GTCGTCGGACTGGTGGACGA-3' (SEQ ID NO: 5) as a sense primer and 5'-CCCAGAGCGTGGTAGTCTGC-3' (SEQ ID NO: 6) as an antisense primer respectively. These are also preferably used.

(2) Amplification by RT-PCR using a Mouse Total RNA as a Template

A total RNA can be obtained by a known method (e.g., Kingston, R. S., (1991) in Current Protocols in Molecular Biology, Suppl. 14, Unit 4.2, Greene Publishing Associates and Wiley Interscience, New York). Any starting material can be used without limitation as long as it expresses mRNA of the polypeptide of the present invention. For example, mouse embryo, particularly 13-day-old embryo can be used.

A partial cDNA encoding the polypeptide of the present invention can be amplified by RT-PCR using the above total RNA as a template and oligonucleotide primers. PCR can be performed following the usual method.

(3) Screening the DNA of the Present Invention from a Mouse cDNA Library Using the PCR Products The PCR products obtained in RT-PCR of (2) above are labelled with $^{32}P$ or the like, then used as hybridization probes for screening cDNA fragments (the DNA of the present invention) from a cDNA library. The mouse cDNA library to be used is not particularly limited. As an example thereof, a λgt11 library containing mouse embryo cDNA (λgt11 mouse embryo cDNA library) may be exemplified.

Hybridization can be carried out by a known method (e.g., J. Biol. Chem., 270, 18575–18580 (1995)).

A DNA insert is isolated from a positive clone by digestion with EcoRI and subcloned into, for example, pBluescript II SK– (STRATAGENE). Thereafter, the nucleotide sequence can be determined by a known method such as the dideoxy chain termination method (Proc. Natl. Acad. Sci. U.S.A., 74, 5463–5467 (1977)).

The nucleotide sequence of the DNA of the present invention obtained by a series of the above methods and the amino acid sequence deduced from this nucleotide sequence are shown in SEQ ID NO: 1 and the same amino acid sequence alone is shown in SEQ ID NO: 2.

(4) Screening a Human cDNA Library and Sequencing of Nucleotide Sequence Using the (Mouse) cDNA as Obtained Above The human DNA of the present invention can be obtained by screening a human cDNA library (e.g., a λgt11 library containing human fetal brain cDNA) using the (mouse) cDNA as obtained above. The nucleoctide sequence can also be determined by the method as described above.

The nucleotide sequence of the DNA of the present invention obtained by this method and the amino acid sequence deduced from this nucleotide sequence are shown in SEQ ID NO: 3 and the same amino acid sequence alone is shown in SEQ ID NO: 4.

2. The Method of Producing the Polypeptide of the Present Invention using the DNA of the Present Invention Cells into which the DNA of the present invention has been transfected are cultivated in a suitable medium to allow the polypeptide encoded by the DNA of the present invention to be produced and accumulated in the culture. The polypeptide of the present invention can be produced by recovering it from the culture.

The cells into which the DNA of the present invention has been transfected can be obtained by inserting the fragment of the DNA of the present invention into a known expression vector to construct a recombinant plasmid and transfecting the recombinant plasmid into the cells. The DNA of the present invention used herein is not particularly limited as long as it is the DNA of the present invention. It is preferable to use a DNA comprising the nucleotide sequence represented by nucleotide numbers 470 to 1918 in SEQ ID NO: 1 and particularly preferable to use a DNA having the nucleotide sequence represented by nucleotide numbers 467 to 1921 in SEQ ID NO: 1. It is also preferable to use a DNA comprising the nucleotide sequence represented by nucleotide numbers 390 to 1841 in SEQ ID NO: 3 and particularly preferable to use a DNA comprising the nucleotide sequence represented by nucleotide numbers 387 to 1844 in SEQ ID NO: 3.

As the cells, procaryotic cells such as *Escherichia coli* and eucaryotic cells such as mammalian cells may be exemplified. When procaryotic cells such as *Escherichia coli* are used, addition of sugar chain does not occur to the polypeptide produced by expression of the DNA of the present invention, then the polypeptide of the present invention having no sugar chain can be obtained. When eucaryotic cells such as mammalian cells are used, sugar chain may add to the polypeptide produced by expression of the DNA of the present invention, then the form of the polypeptide of the present invention comprising sugar chain can be obtained.

In this producing method, a host-vector system usually used for production of proteins can be used. For example, it is preferable to use a combination of a cultured cell derived from mammals such as COS-7 cells and an expression vector for mammalian cells such as pcDNA3 expression vector (Invitrogen Co.). Culture media and culturing conditions are appropriately selected depending on the host, that is cells, to be used.

The DNA of the present invention may be expressed directly. Alternatively, it may be expressed with another polypeptide as a fusion polypeptide. The full-length DNA of the present invention may be expressed. It may also be expressed in part as a partial peptide.

Recovering the polypeptide of the present invention from the culture product may be performed by known extraction and purification methods for polypeptides. The culture product used herein includes the medium and the cells in the medium.

Specific examples of the method of extracting the polypeptide of the present invention include extraction by disrupting cells such as homogenization, glass beads mill method, sonication, osmotic shock procedure, and freezing and thawing method, extraction with a surfactant, or any combination thereof.

For example, homogenization is preferable when the polypeptide of the present invention is extracted from the above-described culture product.

More specifically, the cells are collected from the culture product, and a buffer (which may contain a surfactant) is added thereto. The resulting cell suspension is homogenized with a homogenizer and then extraction can be performed by separating it into cell residue and a supernatant (extract) by a separation method such as centrifugation and it is preferable.

Specific examples of the method of purifying the polypeptide of the present invention include salting out with salt such as ammonium sulfate or sodium sulfate, centrifugation, dialysis, ultrafiltration, absorption chromatography, ion exchange chromatography, hydrophobic chromatography, reverse phase chromatography, gel filtration, gel permeation chromatography, affinity chromatography, electrophoresis, and any combination thereof.

It can be confirmed whether the polypeptide of the present invention has been produced or not by analyzing amino acid sequence, action, and substrate specificity of the purified polypeptide and comparing with physical properties of the polypeptide of the present invention as described in <1>.

The DNA of the present invention would be expected to used for production of the polypeptide of the present invention in large scale, artificial synthesis of GlyCAM-1 in the living organisms (cells), or the like.

<3> The producing Method 1 of the Present Invention

The producing method 1 of the present invention is a method of producing a sulfated sugar represented by the formula III, which comprises a step of reacting the polypeptide of the present invention with a sugar chain represented by the formula IV.

$$(SO_4\text{-}6)GlcNAc\text{—}R \quad (III),$$

$$GlcNAc\text{—}R \quad (IV),$$

wherein —R represents a hydrogen atom or a sugar residue bonded by a glycosidic linkage.

The polypeptide of the present invention usable in the producing method 1 of the present invention is not particularly limited as long as it is the polypeptide of the present invention. The polypeptide of the present invention usable herein is not necessarily completely purified as long as the activities of the polypeptide are not substantially deteriorated. Thus, the polypeptide partially purified or in the form of the cell extract may also be used.

By the producing method 1 of the present invention, the polypeptide of the present invention has been found to have an enzymatic activity to specifically transfer a sulfate group from a sulfate group donor to a hydroxyl group at 6 position of an N-acetylglucosamine residue located al a non-reducing end. The producing method 1 of the present invention is a method of producing a sulfated sugar utilizing the above finding. The most important and essential element in the production method 1 of the present invention is the part except —R in the above formula III and IV. In other words, —R may have an optional structure and the structure of the sugar residue is not particularly limited. For example, —R may be a sugar chain (glycolipid) having a lipid (such as a ceramide residue) at its end.

The above formulae III and IV are preferably the sugar chains represented by the formulae V and VI, respectively.

$$(SO_4\text{-}6)GlcNAc\beta1\text{-}3Gal\beta1\text{-}4GlcNAc\text{—}R' \quad (V)$$

$$GlcNAc\beta1\text{-}3Gal\beta1\text{-}4GlcNAc\text{—}R' \quad (VI),$$

wherein —R' represents a hydrogen atom or a sugar residue bonded a glycosidic linkage.

R' is preferably a hydrogen atom or a sugar chain having 1 to 15 saccharides, more preferably a hydrogen atom or a sugar chain having 1 to 10 saccharides, particularly preferably a hydrogen atom or a sugar chain having 1 to 2 saccharides, and most preferably a hydrogen atom. When —R' is a sugar chain, it has preferably a backbone composed of a repeating structure of (-3Galβ1-4GlcNAcβ1-) (lactosamine). In this case, a sialic acid residue, a fucose residue, a sulfate group and so on may be added to the backbone of —R.

When the polypeptide of the present invention is reacted with the sugar chain represented by the formula IV in the producing method 1 of the present invention, it is preferable to coexist with a sulfate group donor.

In the producing method 1 of the present invention, PAPS is preferably used as a sulfate group donor.

The reaction to subject the polypeptide of the present invention to the sugar chain represented by the formula IV can be carried out by making coexist with the polypeptide of the present invention, the sugar chain represented by the formula IV, and the sulfate group donor. The pH in this reaction is not particularly limited as long as the activity of the polypeptide of the present invention can be retained. The reaction is preferably performed at around the neutral pH (for example, about pH 6.8), more preferably in a buffer solution having the buffering activity at this pH value. The reaction temperature is not particularly limited as long as the activity of the polypeptide of the present invention can be retained. The temperature from about 30 to 40° C. may be exemplified. Furthermore, when some substance enhances the activity of the polypeptide of the present invention, the substance may be added. One of ordinary skilled in the art would determine the reaction time depending on amounts used of the sugar chain, the sulfate group donor, and the polypeptide of the present invention and other reaction conditions thereof. In the reaction, $MnCl_2$ or the like may coexist.

In the case of small scale production, the polypeptide of the present invention can exist under the coexistence with the sugar chain represented by the formula IV and the sulfate group donor and said polypeptide may be reacted. In the case of large scale production, the polypeptide of the present invention can be continuously reacted by using immobilized enzyme prepared by immobilizing the polypeptide of the present invention with an appropriate solid phase (beads, or the like) or a membrane reactor such as a ultrafiltration membrane, or a dialysis membrane. A bioreactor for regenerating (synthesizing) the sulfate group donor may be used in combination.

By the action of the polypeptide of the present invention, a sulfate group is specifically transfected to a hydroxyl group at 6 position of the N-acetylglucosamine residue located at the non-reducing end of the sugar chain represented by the formula IV to thereby form the sugar chain represented by the formula III.

The sugar chain represented by the formula III can be recovered from the reaction mixture by usual methods for isolating and purifying sugar chains. Examples of such methods include adsorption chromatography, anion exchange chromatography, hydrophobic chromatography, gel filtration, gel permeation chromatography, paper electrophoresis, paper chromatography, thin layer chromatography, fractionation with organic solvents (preferably alcohol, acetone, and the like), and any combination of these methods. However, the recovering methods are not limited thereto.

The thus-obtained sugar chain represented by the formula III can be used as an intermediate for production of, for example, GlyCAM-1 or its sugar chain backbone structure <4> The Producing Method 2 of the Present Invention The producing method 2 of the present invention is a method of producing sulfated sugar which comprises steps of transfecting cells with the DNA of the present invention and then cultivating the cells.

As long as the method includes at least these steps, any method comprising additional steps is included in the producing method 2 of the present invention. For example, the producing method 2 of the present invention includes a method of producing sulfated sugar which comprises cultivating cells transfected with the DNA of the present invention in an appropriate culture medium isolating the cells from the culture product, and collecting sulfated sugar chain expressed on the cells.

The produced sulfated sugar is not necessarily isolated and purified from the cells. When the cells themselves on whose surface sulfated sugar is expressed are desired, the cells are collected in the culture product and used as they are.

The DNA of the present invention can be transfected into cells by a known method using DEAE-dextran, calcium phosphate, polybrene, and the like or the other method well known in genetic engineering field.

The DNA of the present invention to be transfected into cells is preferably transfected into the cells in the form of a recombinant plasmid prepared by inserting the DNA of the present invention into a known expression vector. The DNA of the present invention used herein is not particularly limited as long as it is included in the DNA of the present invention. It is preferable to use a DNA comprising the nucleotide sequence represented by nucleotide numbers 470 to 1918 in SEQ ID NO: 1, particularly a DNA having the nucleotide sequence represented by nucleotide numbers 467 to 1921 in SEQ ID NO: 1.

Procaryotic cells such as *Escherichia coli* and eucaryotic cells such as mammalian cells are exemplified as the cells.

In this producing method, a host-vector system usually used for production of proteins can be used. For example, it is preferable to use a combination of a cultured cell derived from mammals such as COS-7 cells and an expression vector for mammalian cells such as pcDNA3 expression vector (Invitrogen Co.). Culture media and culturing conditions are appropriately selected depending on the host, that is cells, to be used. The culture product can be obtained by performing cultivation under such conditions.

The sulfated sugar may be collected from the culture product by known extraction and purification methods for glycolipids. The culture product used herein includes the medium and the cells in the medium.

Specific examples of the method of extracting glycolipids includes extraction with an organic solvent such as methanol or chloroform, extraction by disrupting cells such as homogenization or sonication, and any combination thereof. The cells in the culture product are subjected to such extraction procedures to obtain extract containing sulfated sugar.

The sulfated sugar can be isolated and purified from the extract by usual methods for isolating and purifying sugar chains. It can be performed by the method such as adsorption chromatography, anion exchange chromatography, hydrophobic chromatography, gel filtration, gel permeation chromatography, paper electrophoresis, paper chromatography, thin layer chromatography, fractionation with organic solvents (preferably alcohol, acetone, and the like), and any combination of these methods. However, the recovering methods are not limited thereto.

Through the step that the hydroxyl group at 6th position of the N-acetylglucosamine residue located at the non-reducing end of the sugar chain is sulfated by the action of the polypeptide of the present invention expressed by transfecting the DNA of the present invention into the cells, the sulfated sugar produced by the producing method 2 of the present invention is expressed on the cell surface. The sulfated sugar expressed has at least a sugar chain structure represented by the formula VII:

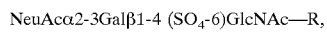

NeuAcα2-3Galβ1-4 (SO$_4$-6)GlcNAc—R, wherein —R represents a hydrogen atom or a sugar residue bonding by a glycosidic linkage. A lipid such as ceramide may be bound to the hydrogen atom or the sugar residue bonding by a glycosidic linkage.

This sugar chain structure is recognized by antibodies that reacts with 6-sulfated sialyl Lewis X ceramide (6-Sulfo SLeX ceramide) and SL2L4 (NeuAcα2-3Galβ1-4(SO$_4$-6)GlcNAcβ1-3(SO$_4$-6)Galβ1-4(SO$_4$-6)GlcNAc) but does not react with 6'-sulfated sialyl Lewis X ceramide (6'-Sulfo SLeX ceramide) and sialylparagloboside (SPG) (the minimum structure necessary for the reaction is NeuAcα2-3Galβ1-4(SO$_4$-6)GlcNAc). Such antibodies can be prepared by usual methods for preparing antibodies using 6-sulfated sialyl Lewis X ceramide. Antibodies are preferably monoclonal antibodies.

The monoclonal antibodies can be prepared by the method of Kohler and Milstein (Nature 256, 495–497 (1975)). For example, 6-sulfated sialyl Lewis X ceramide is allowed to be adsorbed to bacterial cells such as *Salmonella minnesota*. The resulting conjugate is administered to an animal to be immunized such as mice, rats, guinea pigs, rabbits, goats, sheep, and the like, intraperitoneally, subcutaneously, or into footpads. Spleen or popliteal lymph nodes are taken out and cells collected from these tissues are subjected to cell fusion with a tumor cell line, myeloma, to establish hybridoma. The hybridomas thus obtained are subcultured to be selected among these hybridoma continuously producing an antibody that reacts with 6-sulfated sialyl Lewis X ceramide and SL2L4 but does not react with 6'-sulfated sialyl Lewis X ceramide and sialylparaglobcside (an antibody having as the minimum structure necessary for the reaction of NeuAcα2-3Galβ1-4(SO$_4$-6)GlcNAc). The thus-selected cell line is cultured in an appropriate medium and a monoclonal antibody is produced in the medium. Alternatively, the monoclonal antibody can be produced in large scale by culturing the above-described hybridoma in vivo, for example, in abdominal cavity of a mouse. As the cells to be used for cell fusion, lymph node cells and lymphocytes in peripheral blood as well as spleen cells can be used. Myeloma cell line is preferably derived from the same cell line as compared with those derived from heterologous cell line so as to obtain a hybridoma that stably produces antibodies. An example of the antibody includes the G72 antibody as will be described in Examples later.

The sulfated sugar produced by the producing method 2 of the present invention can be confirmed for its production by using the above-described antibody. A known immunological method can be used for confirming the production using the antibody. For example, such a method includes immunoblotting, labeling immunoassay (e.g., EIA, ELISA, radioimmunoassay, fluoroimmunoassay, or the like). When the sulfated sugar expressed on the cell surface is to be confirmed, flow cytometry can also be used. As a matter of course, the sulfated sugar produced by the producing method 2 of the present invention can be confirmed by using a known technique for analyzing sugar chain structures.

In the producing method 2 of the present invention, cDNA encoding fucosyltransferase can be transfected into cells together when the DNA of the present invention is transfected into cells. Thus, the producing method 2 of the present invention includes a method of producing sulfated sugar which comprises steps of transfecting cells with the DNA of the present invention and cDNA encoding fucosyltransferase concurrently and then cultivating the cells.

Fucosyltransferase to be transfected is not particularly limited. It is known that fucosyltransferase IV can form the Lewis X structure (Galβ1-4(Fucα1-3)GlcNAc) by transferring fucose to N-acetyllactosamine (J. Biol. Chem. 2 66, 17467–17477 (1991), Cell 63, 1349–1356 (1990)) and thus is preferably used. The cDNA encoding fucosyltransferase can be inserted into an appropriate expression vector and transfected into cells concurrently with the DNA of the present invention. Preferable expression vectors are those used for the DNA of the present invention.

The sulfated sugar produced by this method is expressed on the cell surface through the process in which the hydroxyl group at 6 position of the N-acetylglucosamine residue located at the non-reducing end of the sugar chain is sulfated by the actions of the polypeptide of the present invention expressed by the DNA of the present invention inserting into the cells, fucosyltransferase and then fucose is transferred to N-acetyllactosarine by the actions of fucosyltransferase expressed by the cDNA of fucosyltransferase inserting into the cells. The expressed sulfated sugar has at least a sugar chain structure represented by the formula VIII;

Galβ1-4(Fucα1-3)(SO$_4$-6)GlcNAc—R    (VIII)

wherein —R represents a hydrogen atom or a sugar residue bonding by a glycosidic linkage. A lipid such as ceramide may be bound to the hydrogen atom or the sugar residue bonding by a glycosidic linkage.

This sugar chain structure is recognized by monoclonal antibodies that specifically react with 6-sulfated Lewis X (Galβ1-4(Fucα1-3) (SO$_4$-6)GlcNAc; 6-Sulfo LeX) structure but do not react with Lewis X (Galβ1-4(Fucα1-3)GlcNAc; LeX) and 6'-sulfated Lewis X ((SO$_4$-6) Galβ1-4(Fucα1-3) GlcNAc; 6'-sulfo LeX) structures. Such antibodies ; can be prepared by usual methods for preparing antibodies using 6-sulfated Lewis X ceramide (Galβ1-4(Fucα1-3)(SO$_4$-6) GlcNAcβ1-3Galβ1-4Glcβ1-Cer). Antibodies are preferably monoclonal antibodies.

The monoclonal antibodies can be prepared by the method as described above. An antigen to be used for immunization is preferably 6-sulfated Lewis X ceramide adsorbed to bacterial cells such as *Salmonella minnesota*.

From the hybridomas prepared by the above method, cell lines continuously producing an antibody that specifically re acts with 6-sulfated Lewis X structure but does not react with Lewis X and 6'-sulfated Lewis X are selected. A monoclonal antibody is obtained in the medium by culturing the thus-selected cell line in an appropriate medium. Alternatively, the monoclonal antibody can be (produced in large scale by culturing the above-described hybridoma in vivo, for example, in abdominal cavity of a mouse. The cells to be used for cell fusion are also the same as described above.

An example of such an antibody includes the AG223 antibody as will be described in Examples later.

The sulfated sugar produced by this method can be confirmed for its production by using the above-described antibody. Confirmation with antibodies can be performed by using known immunological techniques. As a matter of course, it can be confirmed using a known technique for analyzing sugar chain structure. These methods can be explained as described above.

The obtained sugar chains represented by the formulae VII and VIII can be used as intermediates for production of, for example, GlyCAM-1 or its sugar chain backbone structure.

The polypeptide of the present invention is a polypeptide of N-acetylglucosamine-6-O-sulfotransferase having activity to specifically transfer a sulfate group to a hydroxyl group at 6 position of an N-acetylglucosamine residue located at a non-reducing end of a sugar chain. Therefore, it is useful for synthesis of functional sugar chains such as GlyCAM-1 (expected to be used as an anti-inflammatory agent or the like). The DNA of the present invention can be used for synthesis of the polypeptide of the present invention in large scale and artificial expression of functional sugar 2(3 chains such as GlyCAM-1 in the living organism (cells).

The methods 1 and 2 of the present invention is useful as a method of producing functional sugar chains such as GlyCAM-1 or their synthetic intermediates.

DESCRIPTION OF THE PREFERRED EMBODIMENT

Hereinafter, the present invention will be more specifically explained with reference to Examples.

<1> Materials and Methods Commonly used Throughout the Examples (1) Materials $^{35}$S-PAPS(3'-Phosphoadenosine-5'-phosphosulfate; 58.1 GBq/mmol) was from DuPont NEN; $^3$H-NaBH$_4$(16.3 GBq/mmol) and α-$^{32}$P-dCTP (110 GBq/nmol) were from Amersham; chodroitin sulfate A (whale cartilage), chondroitin sulfate C (shark cartilage), dermatan sulfate, completely desulfated and N-resulfated heparin (CDSNS-heparin) and Streptococcus β-galactosidase were from Seikagaku Corporation; unlabeled PAPS, mucin from porcine stomach and mucin from bovine submaxillary gland were from Sigma; Hiload Superdex 30 HR 16/60 and fast desalting column HR 10/10 were from Pharmacia Biotech; Partisil SAX-10 was from Whatman; the mouse day-7 embryo 5'-STRETCH PLUS λgt 11 cDNA library was from CLONTECH; an anti-Lewis X antibody LeuMl was from Becton Dickinson Labware.

Keratan sulfate from bovine cornea and Galβ1-4GlcNAcβ1-3Galβ1-4GlcNAc(sometimes referred to as "L1L1" herein) were from Seikagaku Corporation. Partially desulfated keratan sulfate (sulfate/glucosamine=0.62) was prepared from corneal keratan sulfate as described (J. Biol. Chem., 272, 32321–32328 (1997), J. Biochem. (Tokyo) 86, 1323–1329 (1979)).

GlcNAcβ1-3Galβ1-4GlcNAc was prepared from L1L1 by β-galactosidase digestion. Reaction mixture for β-galactosidase digestion contained 2 mg L1L1, 5 μmole of sodium acetate buffer, pH5.5, and 40 mU enzyme in a final volume of 100 μl (J. Biochem. (Tokyo) 80, 9–17 (1976)). The reaction mixture was incubated at 37° C. for 24 h. After digestion with β-galactosidase, GlcNAcβ1-3Galβ1-4GlcNAc was purified by Superdex 30 chromarograhy and desalted by lyophilization. Galβ1-4-$^3$H-($SO_4$-6)2,5-anhydromannitol and ($SO_4$-6)2,5-$^3$H-anhydromannitol were obtained from keratan sulfate by reaction sequence of N-deacetylation, deamination, $NaB^3H_4$ reduction and partial acid hydrolysis (Glycobiology, 6, 51–57 (1996), Biochem. J. 235, 225–236 (1986)).

Structere of synthetic glycolipids used in the examples as follows; sialyl Lewis X ceramide=NeuAcα2-3Galβ1-4 (Fucα1-3)GlcNAc β1-3Galβ1-4Glcβ1-Cer; 6-sulfo sialyl Lewis X ceramide=NeuAcα2-3Galβ1-4(Fucα1-3)($SO_4$-6) GlcNAcβ1-3Galβ1-4Glcβ1-Cer; 6'-sulfo sialyl Lewis X ceramide=NeuAcα2-3($SO_4$-6)Galβ1-4(Fucα1-3) GlcNAcβ1-3Galβ1-4Glcβ1-Cer; 6,6'-bis-sulfo sialyl Lewis X ceramide=NeuAcα2-3($SO_4$-6) Galβ1-4(Fucα1-3) ($SO_4$-6)GlcNAcβ1-3Galβ1-4Glcβ1-Cer (Carbohydr. Res., 209, c1–c4 (1991), Carbohydr. Res., 285, c1–c8 (1996), J. Med. Chem., 39, 1339–1343 (1996)). These glycolipids were generous gifts from Dr. Makoto Kiso, Faculty of Agriculture, Gifu University. The asialo compounds were prepared from the corresponding synthetic glycolipids by digestion with neuraminidase from Arthrobacter ureafaciens (Nakarai Tesque Co.). The sialylated paraglobosides (NeuAcα2-3Galβ1-4GlcNAcβ1-3Galβ1-4Glcβ1-Cer and NeuAcα2–6Galβ3-4GlcNAcβ1-3Galβ1-4Glcβ1-Cer) were prepared from human colon and liver carcinoma tissues. NeuAcα2-3Galβ1-4($SO_4$-6)GlcNAcβ1-3($SO_4$-6)Galβ1-4 ($SO_4$-6)GlcNAc (sometimes referred to as "SL2L4" herein) and GlcNAcβ1-3Galβ1-4GlcNAcβ1-3Galβ1-4GlcNAc were generous gifts from Dr. Keiichi Yoshida (Seikagaku Corporation). The former was coupled to cholesteryl aniline through reductive amination (Blood, 82, 2797–2805 (1993)).

(2)Isolation of the DNA of the Present Invention (2-1)Isolation of the DNA of the Present Invention Derived from Mouse A mouse expressed sequence tag (EST) sequence (Genbank accession number AA103962) with similarity to the catalytic portion of mouse chondroitin 6-sulfotransferase was amplified by the RT-PCR method using mouse day-13 embryo total RNA as a template. The sense primer, GCGTCGGACTGGTGGACGA (SEQ ID NO:5) and the antisense prime, CCCAGAGCGTGGTAGTCTGC (SEQ ID NO:6), were used for PCR amplification, which was carried out at 94° C. for 3 min, with 35 cycles of 94° C. for 0.5 min, 60° C. for 1 min and 72° C. for 1 min. The PCR product (368 bp) was $^{32}$P-labeled with a Megaprime™ DNA labeled kit (Amersham CD.) and was used to screen the λgt 11 mouse day-7 embryo cDNA library.

Hybridization was carried out as described (J. Biol. Chem., 270, 18575–18580 (1995)). DNA insert was isolated from positive λgt11 clones by digestion with EcoRI and was subcloned into the pBluescriptII SK– (STRATAGENE Co.). Then, the nucleotide sequence was determined by the dideoxy chain termination method (Proc. Natl. Acad. Sci. U.S.A., 74, 5463–5467 (1977)) using an Applied Biosystems automated sequencer.

(2—2) Isolation of the Human DNA of the Present Invention

The DNA of the present invention derived from mouse as obtained above was labeled with $^{32}$P using Megaprime DNA labeling systems (Amersham Co.). Using this as a probe, the λgt11 library containing cDNA of human fetal brain (CLONTECH CO.) was screened. Hybridization was carried out by the method described in J. Biol. Chem. 272, 32321–32328 (1997).

A DNA insert was isolated from positive λgt11 clones by digestion with EcoRI and subcloned into pBluescript II SK– (STRATAGENE CO.). The nucleotide sequence was determined by the method used for the above-described DNA of the present invention derived from mouse.

(3) Construction of Expression Vectors

A cDNA fragment encoding the open reading frame of the polypeptide of the present invention (the DNA of the present invention derived from mouse) was amplified by PCR using the cloned cDNA fragment from mouse as a template. The sense primer, ACGAATTCGGGATGAAGGTATTTCG-CAGG (SEQ ID NO:7), and the antisense primer, ATGAAT-TCTCAAAGCCGGGGCTTCCTGAG (SEQ ID NO:8), were used for PCR amplification, which was carried out at 94° C. for 3 min, with 35 cycles of 94° C. for 1 min, 60° C. for 1 min and 72° C. for 2 min in 5% (v/v) dimethylsulfoxide. The PCR product including the open reading frame of polypeptide of the present invention (nucleotide numbers 467 to 1921 in SEQ ID NO:1) was digested with EcoRI and subcloned into the pcDNA3 expression vector (Invitrogen Co.). Recombinant plasmids containing the DNA fragment in the correct orientation, pcDNA3-GlcNAc6ST, was used for expression. The recombinant plasmids containing the DNA fragment in the reverse orientation, pcDNA3-GlcNAc6STA, was used in control experiments.

An expression vector was constructed in the same manner as described above using the DNA of the present invention derived from human. First, PCR was carried out using CTGAATTCGGAATGKAGGTGTTCCGTA (SEQ ID NO: 9) and GAGAATTCTTAGAGACGGGGCTTCCGA (SEQ ID NO: 10) as primers, and the cloned human cDNA fragment as a template to obtain PCR products (nucleotide numbers 387 to 1844 in SEQ ID NO: 3) containing an open reading frame of the polypeptide of the present invention. The PCR products was digested with EcoRI and subcloned into the expression vector, pcDNA3. A recombinant plasmid (pcDNA3-hGlcNAc6ST) containing the DNA fragment in the correct orientation was used for expression, while a recombinant plasmid (pcDNA3-hGlcNAc6STA) containing the DNA fragment in the reverse orientation was used as control.

Previously cloned 1544 bp fragment of the mouse fucosyltransferase IV gene (J. Biochem. (Tokyo) 119, 302–308 (1996)) was subdcloned into the BamHI and EcoRI sites of the pcDNA3 expression vector as described above. The recombinant plasmid containing the DNA fragment in the correct orientation, pcDNA3-FucTIV, was used.

(4) Transient Expression of the DNA of the Present Invention in COS-7 Cells

COS-7 cells ($3 \times 10^6$ cells in a 10 cm-dish, from Riken cell bank) were transfected with 15 μg of expression plasmids by the DEAE-dextran method (Aruffo, A. (1991) in Current Protocols in Molecular Biology, Suppl.14, Unit 16.13, Greene Publishing Associates and Wiley Interscience, New York). After 65 h culture in Dulbecco-modified minimum essential medium containing 10% fetal calf serum, the cells were washed with phosphate buffered saline(PBS) and scraped off the dishes. These cells were collected and homogenized with a Dounce homogenizer in 1.5 mL/dish of 0.25 M sucrose, 10 mM Tris-HCl, pH 7.2, and 0.5% Triton X-100. The homogenates were centrifuged at 10,000×g for 15 min, and the supernatant was saved. This supernatant is hereinafter referred to as "extracts". For FACS (fluorescence-activated cell sorter) analysis, the transfected cells were cultured for 48 h, transferred into 25 cm² culture flasks ($3 \times 10^5$ cells per flask) and further cultured for 36 h.

(5) Assay of Sulfotransferase Activity to Various High Molecular Weight Substrates Sulfotransferase activities were assayed using various glycosaminoglycans as substrates (acceptors) as described (J. Biol. Chem., 272, 32321–32328 (1997)). When mucins were used as acceptors, reaction mixture containing 2.5 μmol of imidazole-HCl, pH 6.8, 0.25 μmol of $CaCl_2$, 0.1 μmol of dithiothreitol, 0.1 μmol of NaF, 0.1 μmol of AMP, 2.0 μg of mucins, 50 pmol of $^{35}$S-PAPS (about $5.0 \times 10^5$ cpm), and 5 μl of the extracts in a final volume of 50 μl was incubated at 37° C. for 1 h.

After isolation with a fast desalting column, radioactivity incorporated onto mucins was determined.

(6) Assay of Sulfotransferase Activity to Oligosaccharides

The reaction mixture contained 2.5 μmol of imidazole-HCl, pH 6.8, 0.5 μmol of $MnCl_2$, 0.1 μmol of AMP, 1.0 μmol of NaF, 25 nmol of oligosaccharides, 50 pmol of $^{35}$S-PAPS (about $5 \times 10^5$ cpm), and 5 μl of the extracts in a final volume of 50 μl. The reaction mixture was incubated at 30° C. for 5 h and the reaction was stopped by immersing the reaction tubes in a boiling water bath for 1 min. $^{35}$S-Labeled oligosaccharides were separated from $^{35}SO_4$ and $^{35}$S-PAPS by Superdex 30 gel chromatography, and the radioactivity was determined. When GlcNAcβ1-3Galβ1-4GlcNAc was used as an acceptor, sulfotransferase reaction proceeded linearly up to 5 h under the assay conditions.

(7) Superdex 30 Chromatography, Paper Electrophoresis, Paper Chromatography, HPLC and TLC Hiload Superdex 30 16/60 column was equilibrated with 0.2M $NH_4HCO_3$. The flow rate was 1 ml/min. One ml fractions were collected and mixed with 4 ml Cleasol (Nakarai fesque Co.), and the radioactivity was determined. Oligosaccharides were monitored by absorption at 210 nm. Paper electrophoresis was carried out on Whatman No.3 paper(2.5 cm×57 cm) in pyridine/acetic acid/water (1:10:400, by volume, pH 4) at 30 V/cm for 40 min. Samples for paper chromatography was spotted on a Whatman No.3 paper (2.5 cm×57 cm) and developed with 1-butanol/acetic acid/1M $NH_4OH$ (3:2:1, by volume). The dried paper strips after paper electrophoresis or paper chromarography were cut into 1.25 cm segment, and radioactivity was determined by liquid scintillation counting. HPLC analysis of $^{35}$S-labeled product obtained from $^{35}$S-labeled sulfated GlcNAcβ1-3Galβ1-4GlcNAc was carried out on a Partisil SAX-10 column (4.5 mm×25 cm) equilibrated with 5 mM $KH_2PO_4$. The column was developed with 5 mM $KH_2PO_4$. The flow rate was 1 ml/min and the column temperature was 40° C. Fractions, 0.5 ml, were collected and mixed with 4 ml Clearsol, and the radioactivity was determined. TLC was performed on aluminum sheets precoated with cellulose 0.1 mm thick (Merck Co.) in ethyl acetate/pyridine/tetrahydrofuran water/acetic acid (50:22:15:15:4, by volume) (Biochem. J., 319, 209–216 (1996)).

(8) N-Deacetylation, Deamination and $NaBH_4$ Reduction of the $^{35}$S-labeled Sulfated GlcNAcβ(1-3Galβ1-4GlcNAc The $^{35}$-S-labeled sulfated GlcNAcβ1-3Galβ1-4GlcNAc was prepared using the expressed polypeptide of the present invention (2.1 μg as protein in the extract) as described above except that concentration of $^{35}$S-PAPS was increased to 6-fold and incubation was carried out for 25 h. The $^{35}$S-labeled sulfated GlcNAcβ1-3Galβ1-4GlcNAc eluted from the Superdex 30 column was lyophilized, purified by paper electrophoresis and deacetylated with 70% hydrazine containing 1.0% hydrazine sulfate at 95° C. for 6 h (Anal. Biochem. 176, 96–104 (1989)). The deacetylated materials were purified by Superdex 30 chromatography, subjected to deamination with nitrous acid at pH 4 and reduced by $NaBH_4$ (Biochem. J. 235, 225–236 (1996)). Finally the sample was dissolved in 60 μl of water and subjected to paper chromatography.

(9) Immunological Methods

A hybridoma cell line, AG223, which secreted murine IgM monoclonal antibody (AG223) reactive with 6-sulfo Lewis X(Galβ1-4(Fucα1-3) $(S)_4$-6)GlcNAc) was generated according to the method described by Kohler and Milstein (Nature 256,495–497(1975)), and subsequently used to produce anti-carbohydrate antibodies (Kannagi, R., and Hakomori, S. (1980) in Handbook of Experimental Immunology, Vol.4, Applications of immunological methods in biomedical sciences (Weir, D. M., Herzenberg, L., Blackwell, C., and Herzenberg, L. A., eds) pp.117.1–117.20, Blackwell Scientific Pub. Inc., Boston). Briefly, 6-sulfo Lewis X ceramide(Galβ1-4(Fucα1-3) $(SO_4$-6) GlcNAcβ1-3Galβ1-4Glcβ1-Cer) was adsorbed to *Salmonella minnesota* R595 strain and used for repeated intraperitoneal immunization of BALB/c mice on day 0(5 μg glycolipid), day 3 (10 μg), day 7(15 μg), day 12(20 μg), day 17(25 μg) and day 31(35 μg). Three days after the final immunization, the spleen cells were harvested and fused with mouse myeloma p3/X63-Ag8U1. The same glycolipid was used as the antigen in ELISA as used for hybridoma culture supernatants for the cloning procedures. ELISA was performed using glycolipid antigens immobilized at the bottom of 96-well culture plates by the standard method (Hakomori, S., and Kannagi, R., (1986) in Handbook of Experimental Immunology, Vol.1, Immunochemistry(Weir, D. M., Herzenberg, L., Blackwell, C., and Herzenberg, L. A., eds) pp.9.1–9.39, Blackwell Scientific Pub. Inc., Boston). Peroxidase-conjugated goat anti-mouse IgM (μ-chain specific, Cappel Inc.) was used as the second antibody.

A hybridoma cell line G72, which secreted murine IgM monoclonal antibody (G72) reacting with 6-sulfo sialyl N-acetyllactosamine (NeuAcα2-3Galβ1-4($SO_4$-6) GlcNAc) structure was similarly prepared using 6-sulfo sialyl Lewis X ceramide.

Mouse IgM monoclonal antibody (G152) that reacts with 6-sulfated sialyl Lewis X ceramide but does not react with 6'-sulfated sialyl Lewis X ceramide, 6,6'-bis-sulfated sialyl Lewis X ceramide, 6-sulfated Lewis X ceramide, Lewis X ceramide, or the like (thus recognizes 6-sulfated sialyl Lewis X antigen) was prepared using 6-sulfated sialyl Lewis X ceramide as an antigen by the method described in J. Biol. Chem. 273, 11225–11233 (1998).

CSLEX-1 monoclonal antibody (Cancer Res. 44, 5279–5285 (1984)); reacting with sialyl Lewis X antigen) was used to detect sialyl Lewis X antigen.

Cell-surface expression of antigenic epitopes was surveyed by FACS as described in (Biochem. Biophys. Res. Commun., 230, 546–551 (1997)) using a FACScan (Becton Dickinson Co.).

(10) Northern and Genomic Southern Blot Analyses (10-1) Mouse

Total RNA (20 μg) was prepared from C57 BL/6J mouse tissues as described (Anal. Biochem. 162, 156–159 (1987)). Genomic DNA (10 μg) prepared from murine D3 embryonic stem cells (J. Embryol. Exp. Morphol., 87, 27–45 (1985)) was digested for 4 h with appropriate restriction enzymes. The radioactive probe was the same as that used for screenig of the mouse day-7 embryo cDNA library. The blots were washed at 55° C. in 2×SSPE, 0.1% SDS, and finally in 0.1×SSPE, 0.1% SDS at 55° C. The membranes were exposed to a BAS-imaging plate and then the radioactivity on the membrane was determined with a BAS 2000 radio-image analyzer (Fuji Film Co.).

(10-2) Human

Total RNA was prepared from human tissues in the same manner as in (10-1) above. Bpu1102 I-BamHI 368 bp fragment (nucleotide numbers 910 to 1277 in SEQ ID NO: 3) of the DNA of the present invention derived from human was used as a probe. Blotting was carried out in the same manner as in (10-1) above.

(11) In Situ Hybridization

Specimens from C57 BL/6J mice were subjected to hematoxylin-eosin staining or in situ hybridization. As the probe for the polypeptide of the present invention, a 0.6 kbp Pst I fragment of the cDNA (nucleotide numbers 962 to 1561 in SEQ ID NO:1) was subcloned into pBluescript II SK–. Sense and antisense cRNA probes were prepared by in vitro transcription with a DIG RNA labeling kit(Boehringer Mannheim Co., Germany).

(12) Fluorescence in situ Hybridization Analysis

Fluorescence in situ hybridization (FISH) analysis was carried out in accordance with the method described in Genomics, 17, 514–515 (1993) using the DNA of the present invention derived from human (nucleotide numbers 1 to 2409 in SEQ ID NO: 3) as a probe.

<2> RESULTS (1) Cloning of the DNA of the Present Invention

Figure 1:
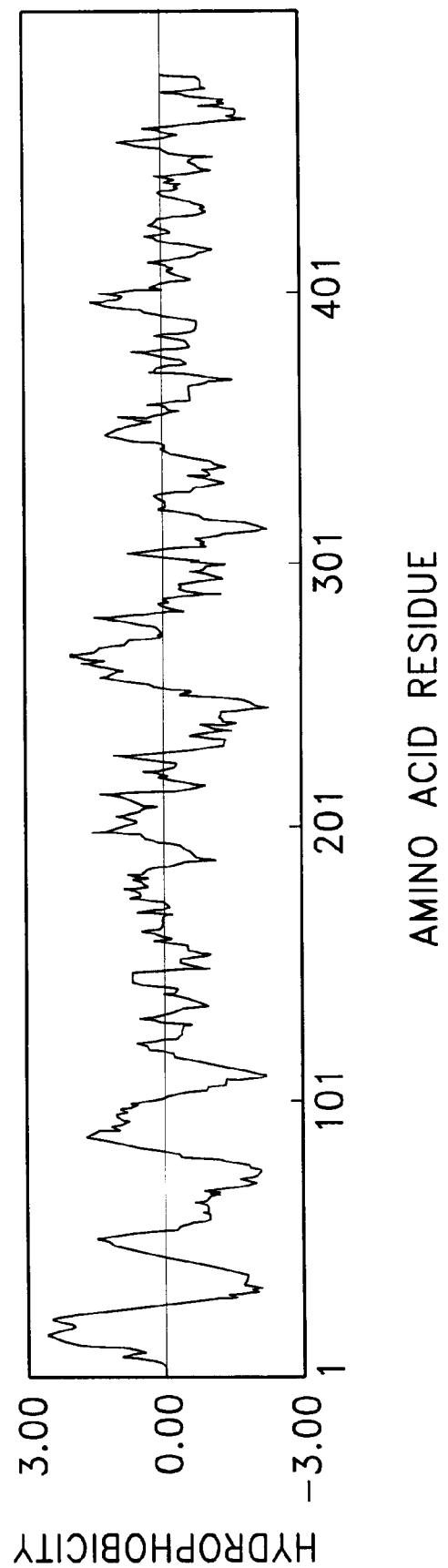
FIG. 1 shows the hydropathy plot of the polypeptide of the present invention derived from mouse. The hydropathy plot was calculated by the method of Kyte and Doolittle (J. Mol. Biol., 157, 105–132 (1982)) with a window of 11 amino acids.

Mouse chondroitin 6-sulfotransferase had cloned previously. By searching in the EST database, we found a small sequence with similarity to the catalytic portion of mouse chondroitin 6-sulfotransferase (Genbank accession number AA103962). We obtained the corresponding cDNA fragment by RT-PCR (nucleotide numbers 1139 to 1506 in SEQ ID NO:1). Approximately 8×10$^5$ plaques of a mouse day-7 embryo cDNA library were screened using the cDNA fragment as a probe, and six independent clones were obtained. The nucleotide sequence of the largest cDNA insert(2.2 kb) was determined (SEQ ID NO:1). The determined 2150-bp cDNA had a single open reading frame consisting of 483 amino acids, with a molecuLar mass of 52829 Da and four potential N-linked glycosylation sites(SEQ ID NO:1). The sequence around the first ATG codon fitted Kozak's rule (Cell, 44, 283–292 (1986)), and the upstream region contained an in-frame stop codon. Hydropathy plot analysis indicated the presence of one prominent hydrophobic segment 20 residues in length in the amino-terminal region (Ala$^8$-Leu$^{27}$), predicting that the polypeptide of the present invention is type II transmembrane protein (FIG. 1). The polypeptide of the present invention showed 25% and 27% homology with mouse chondoroitin 6-sulfotransferase and human keratan sulfate Gal-6-sulfotransferase, respectively. However, no significant homology in amino acid sequence was observed between the protein and other known sulfotransferase (J. Biol. Chem., 267, 15744–15750 (1992), J. Biol. Chem., 272, 13980–13985 (1997), J. Biol. Chem., 272, 28008–28019 (1997), J. Biol. Chem., 272, 29942–29946 (1997), J. Biol. Chem., 272, 4864–486 8 (1997)).

The DNA of the present invention derived from human (SEQ ID NO: 3) was obtained by screening the λgt11 library containing cDNA of human fetal brain using the DNA represented by SEQ ID NO: 1. The obtained DNA consisted of 2409 bp and contained a single open reading frame consisting of 484 amino acid residues (SEQ ID NO: 3). Hydropathy plot analysis suggested that this polypeptide is type II transmembrane protein having transmembrane domain at the amino terminal region.

The sequence in the vicinity of the first ATG codon was in agreement with the Kozak's rule (Cell, 44, 283–292 (1986)).

Another ATG codon exists 41 nucleotide numbers upstream from the first ATG codon. The sequence in the vicinity of this ATG codon was also in agreement with the Kozak's rule. This ATG codon was also found in the corresponding position in the DNA of the present invention derived from mouse. There is no termination codon between the first ATG codon and this ATG codon in the human nor the mouse DNA. Therefore, both of the above two ATG codons can function as an initiation codon in the DNA of the present invention.

The amino acid sequence of the polypeptide encoded by the DNA of SEQ ID NO: 1 and the amino acid sequence of the polypeptide encoded by the DNA of SEQ ID NO: 3 are shown by SEQ ID NO: 2 and SEQ ID NO: 4, respectively. Homology between SEQ ID NO: 2 and SEQ ID NO: 4 was 85% or more.

Figure 2:
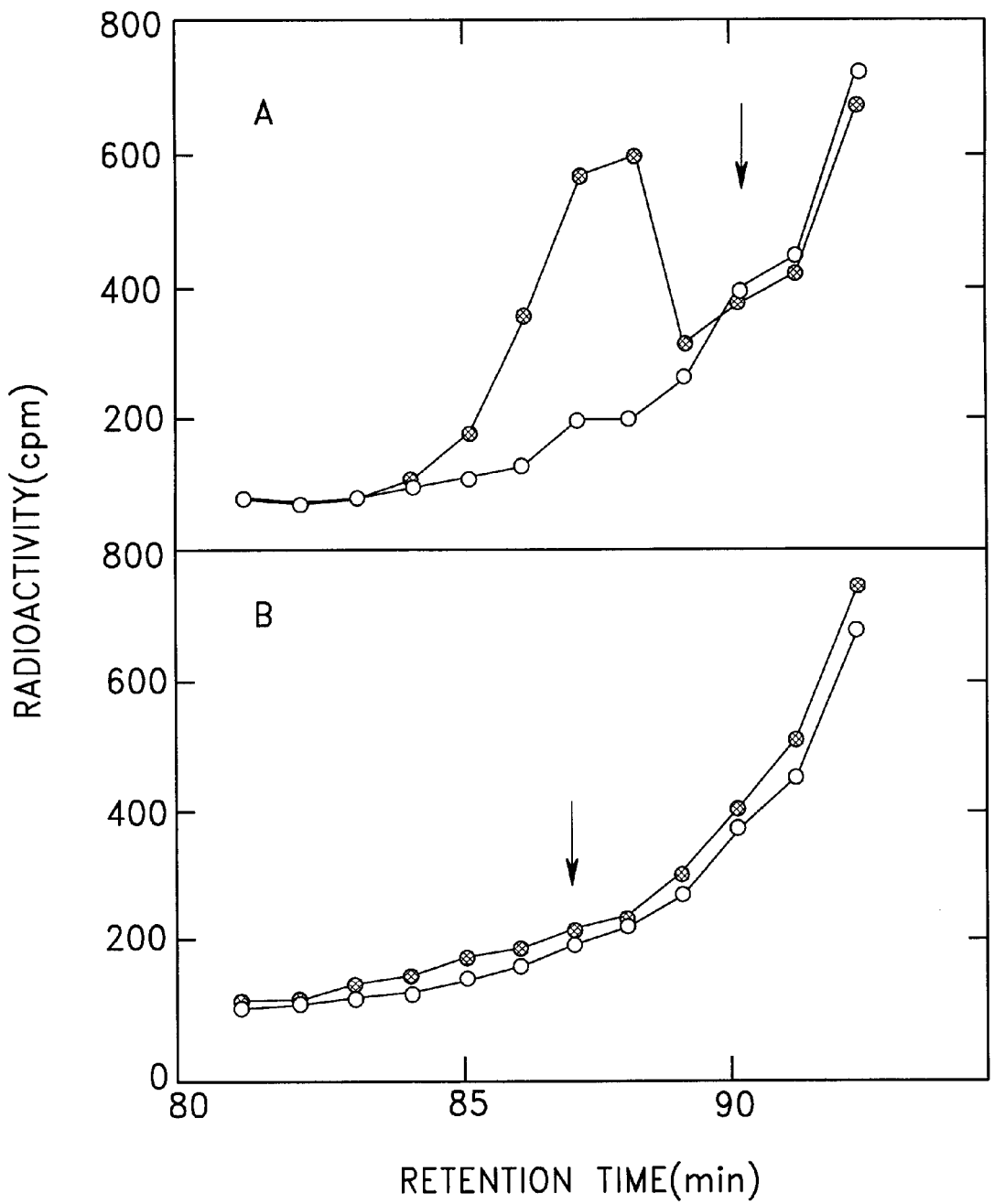
FIGS. 2A and B. shows the substrate specificity of the DNA of the present invention derived from mouse.

(2) Expression of the Polypeptide of the Present Invention from the DNA of the Present Invention The DNA of the present invention, from which the bulk of the 5'- and 3'-non-coding regions was removed, nucleotide numbers 467 to 1921 in SEQ ID NO:1) was inserted into a mammalian expression vector pcDNA3 and overexpressed in CCS-7 cells. Extracts of the transfected cells were assayed for sulfotransferase activity using $^{35}$S-labeled PAPS as the sulfate group donor and various glycoconjutages as sulfate group acceptors: chondroitin, chondroitin 4-sulfate, chondroitin 6-sulfate, dermantan sulfate, keratan sulfate, desulfated keratan sulfate, CDSNS-heparin, mucin from porcine stomach and mucin from bovine submaxillary gland did not serve as acceptors. We examined GlcNAcβ1-3Galβ1-4GlcNAc as a sulfate group acceptor. Superdex 30 chromatography of the reaction mixture indeed revealed a radioactive peak in cells transfected with a vector(pcDNA3-GlcNAc6ST) containing the cDNA of the correct orientation (sense DNA) slightly larger than the acceptor, indicating that the acceptor was sulfated (FIG. 2A). The extract from untransfected cells or those transfected with a vector (pcDNA3-GlcNAc6STA) containing the cDNA of the reverse orientation(the antisense cDNA) showed much less sulfotransferase activity (Table 1). The activity was calculated from the radioactivity contained in Fraction Number 85 to 89 in Superdex 30 chromatography (FIG. 2A). Values are shown that values obtained in the absence of the acceptor were subtracted from the value obtained in the presence of the acceptor. Values of averages ±S.D. of triplicate culture are shown.

TABLE 1

| Vector | Sulfotransferase activity pmole/hour/mg protein |
|---|---|
| None (untransfected) | 1.1 ± 0.7 |
| Sense cDNA | 10.6 ± 2.4 |
| Antisense cDNA | 1.8 ± 0.9 |

In contrast, Galβ1-4GlcNAcβ1-3Galβ1-4GlcNAc did not serve as an acceptor(FIG. 2B). Therefore, it was confirmed that the polypeptide of the present invention transferred sulfate group to GlcNAcβ1-3Galβ1-4GlcNAc, but didn't to Galβ1-4GlcNAcβ1-3Galβ1-4GlcNAc.

COS-7 cells were transfected with the DNA of the present invention from which the bulk of 5'- and 3'-non-coding region was removed (nucleotide numbers 387 to 1844 in SEQ ID NO:3) in the same manner as described above and the extracts of resulting transfectants were examined for its sulfotransferase activity (using GlcNAcβ1-3Galβ1-4GlcNAcβ1-3Galβ1-4GlcNAc as a sulfate group acceptor) in the same manner as described above. As a result, the cells transfected with the vector (pcDNA3-hGlcNAc6ST) containing the cDNA with the correct orientation (sense cDNA) exhibited fivefold or more as high sulfotransferase activity as untransfected cells or the cells transfected with the vector (pcDNA3-hGlcNAc6STA) containing the cDNA with the reverse orientation (antisense cDNA) (Table 2). The activity was calculated from radioactivity of fractions obtained by Superdex 30 chromatography. Values were shown that values obtained in the absence of the acceptor were subtracted from the value obtained in the presence of the acceptor. Values of averages ±S.D. of triplicate culture are shown.

TABLE 2

| Vector | Sulfotransferase activity pmole/hour/mg protein |
|---|---|
| None (untransfected) | 1.33 ± 0.62 |
| Sense cDNA | 6.67 ± 0.51 |
| Antisense cDNA | 1.29 ± 0.23 |

(3) Determination of the Position Where a Sulfate Group is Transferred by the Polypeptide of the Present Invention (Method for measuring the activity of the polypeptide of the present invention)

To determine the position to which $^{35}SO_4$ was transferred to GlcNAcβ1-3Galβ1-4GlcNAc, we degraded the radioactive product by a reaction sequence of N-deacetylation, deamination, and $NaBH_4$ reduction. After degradation, two radioactive products were detected on the paper chromatogram (FIG. 3A). The faster moving peak migrated to the position of $(SO_4-6)2,5$-anhydromannitol. The slower moving teak was thought to be undegraded materials due to incomplete deacetylation because the proportion of the slower moving peak was decreased when $^{35}$S-labeled GlcNAcβ1-3Galβ1-4GlcNAc was subjected to prolonged hydrazinolysis reaction. When the faster migrating material was analyzed by HPLC, $^{35}$S-radioactivity was co-eluted with $(SO_4-6)^3H$-2,5-anhydromannitol (FIG. 3B). The $^{35}$S- and $^3$H-radioactivities also co-migrated upon TLC, using a solvent system which can separate 6-sulfo 2,5-anhydromannnitol from 4-sulfo or 3-sulfo 2,5-anhydromannitol(Biochem. J.,319, 209–216 (19 96)). These results indicate that $^{35}SO_4$ was transferred to position 6 of GlcNAc residue located at the non-reducing end of GlcNAcβ1-3Galβ1-4GlcNAc. Therefore, the cloned DNA of the present invention was found to encode the polypeptide of the present invention.

(4) Expression of Sulfated Sugar by Transfecting the DNA of the Present Invention into Cells Expression of a new antigenic epitope was examined in COS-7 cells trans fected with the DNA of the present invention derived from mouse. For analysis of expression of sulfated sialyl-N-acetyllactosamine structure, we used G72 antibody. It reacted with 6-sulfo sialyl Lewis X ceramide as well as SL2L4, but not with 6'-sulfo sialyl Lewis X ceramide or sialyl-paraglobosides (FIG. 4), indicating that the minimum structure required for the reactivity of the antibody was NeuAcα2-3Galβ1-4($SO_4$-6)GlcNAc. COS-7 cells transfected with the DNA of the present invention expressed the G72 antigen (FIG. 5B). The untransfected cells (FIG. 5A) or the cells transfected with the antisense cDNA (FIG. 5C) were not reactive with the antibody. Neuraminidase digestion abolished the antigenicity (FIG. 5E). Thus, we reached to a conclusion that the polypeptide of the present invention is involved in synthesis of NeuAcα2-3Galβ1-4($SO_4$-6) GlcNAc antigen.

In order to obtain further evidence that the polypeptide of the present invention is involved in formation of 6-sulfo N-acetyllactosamine structure, we doubly transfected COS-7 cells with the DNA of the present invention derived from mouse and the cDNA of fucosyltransferase IV. The latter enzyme is known to be able to form Lewis X structure (Galβ1-4(Fucα1-3)GlcNAc) by transferring fucose to N-acetyllactosamine (J. Biol. Chem., 266, 17467–17477 (1991), Cell, 63, 1349–1356 (1990)). To monitor the cell surface change due to transfection, we used monoclonal antibody AG223, which specifically reacted with 6-sulfo Lewis X structure(Galβ1-4(Fucα1-3) ($SO_4$-6)GlcNAc), and did not react with Lewis X(Galβ1-4(Fucα1-3)GlcNAc) nor with 6'-sulfo Lewis X structure(($SO_4$-6)Galβ1-4(Fucα1-3) GlcNAc) (FIG. 4). Transfection with the DNA of the present invention and the cDNA of fucosyltransferase indeed yielded cells positive for the 6-sulfo Lewis X antigen (FIG. 6C), but cells transfected only with one cDNA did not (FIGS. 6A, B). When the cells were transfected with only the cDNA of fucosyltransferase,the cells became positive for Lewis X antigen (FIG. 6D). Furthermore, expression of new antigenic epitope in COS-7 cells transfected with the DNA of the present invention derived from human was examined.

Expression of sulfated sugar on the cell surface was examined in the same manner as described above using the CSLEX-1 antibody (Cancer Res., 44, 5279–5285 (1984); reacting with sialyl Lewis X antigen), the G72 antibody, and the G152 antibody (which reacted with 6-sulfated sialyl Lewis X ceramide but did not react with 6'-sulfated sialyl Lewis X ceramide, 6,6'-bis-sulfated sialyl Lewis X ceramide, 6-sulfated Lewis X ceramide, Lewis X ceramide, or the like). The results are shown in FIG. 7.

As a result, untransfected cells did not react with any of the antibodies. The cells transfected with cDNA of fucosyltransferase alone reacted with only CELEX-1 antibody. The cells transfected with the DNA of the present invention derived from human reacted with only the G72 antibody. The cells cotransfected with the DNA of the present invention derived from human and the cDNA of fucosyltransferase reacted with any of the CSLEX-1 antibody, the G72 antibody, and the G152 antibody.

These results indicated that sulfated sugar having 6-sulfated sialyl-N-acetyllactosamine structure could be produced by transfecting the DNA of the present invention into cell, and that sulfated sugar having 6-sulfated sialyl Lewis X structure could be produced by concurrently transfecting the DNA of the present invention and cDNA of fucosyltransferase into cells.

(5) Northern Blot and Southern Blot Analyses

The result of the examination using the adult mouse organs (cerebellum, cerebrum, eyeball, heart, lung, muscle, spleen, thymus, liver, pancreas, kidney, stomach, intestine, uterus, ovary, and testis) indicated that the polypeptide of the present invention was strongly expressed in the cerebrum, cerebellum, eye, lung and pancreas (FIG. 8A). Moderate signal was also detected in the intestine, uterus, ovary, mesentric lymph nodes and peripheral (FIG. 8A). The size of major transcript was 3.9 kb. On southern blots, a single band was reacted with the probe after digestion with EcoRI, RcoRV or SacI, indicating that the polypeptide of the present invention was a single copy gene (FIG. 8B).

As a result of examining human tissues (heart, brain, placenta, lung, liver, skeletal muscle, kidney, pancreas, spleen, thymus, prostate, testis, ovary, intestine, colon, peripheral blood lymphocytes, stomach, thyroid gland, spinal cord, lymph node, trachea, adrenal body, and bone marrow), the polypeptide of the present invention was strongly expressed in bone marrow, peripheral blood lymphocytes, spleen, brain, spinal cord, ovary, and placenta. Moderate signal was observed in lymph node, thymes, heart, lung, trachea, stomach, intestine, colon, thyroid gland, prostate, and adrenal body. The size of major transcription products was 3.6 kb.

(6) In Situ Hybridization Analyses

In situ hybridization was performed to determine the expression sites of the polypeptide of the present invention. In the adult mouse brain, strong signals were detected in pyramidal cells in the CA3 subregion of the hippocampus, cerebellar nucleus and Purkinje cells. Moderate signals were detected in the other subregions including CA1 subregion of the hippocampus, thalamus, pontine nucleus, olfactory tubercle and olfactory bulb.

Mesentric lymph nodes were used to disclose the localization of the DNA transcripts in lymphoid tissues. HEV (high endothelial venules), where the ligand for L-selectin is located (J. Cell Biol., 113, 1213–1221 (1991)), are present in the paracortex. They have a cuboidal endothelium with fairly large oval nuclei and a few cytoplasm. The polypeptide of the present invention was specifically expressed on these endothelium.

(7) Fluorescence in situ Hybridization Analysis

Fluorescence in situ hybridization analysis was carried out to determine the position of the DNA of the present invention derived from human on the chromosome. As a result, the DNA of the present invention derived from human was found to locate at the chromosome 7q31 site.

What is claimed is:

1. An isolated polynucleotide encoding a polypeptide comprising the amino acid sequence of SEQ ID NO: 2 or fragment thereof, wherein the polypeptide has an enzymatic activity to transfer a sulfate group from a sulfate group donor to a hydroxyl group at position 6 of an N-acetylglucosamine residue located at a non-reducing end of an oligosaccharide represented by the formula:

GlcNAcβ1-3Galβ1-4GlcNAc wherein GlcNAc represents an N-acelylglucosamine residue, Gal represents a galactose residue, β1-3 represents a β1-3 glycosidic linkage, and β1-4 represents a β1-4 glycosidic linkage.

2. An isolated polynueleotide comprising a nucleotide sequence represented by nucleotide numbers 470 to 1918 in SEQ ID NO: 1.

3. An isolated polynucleotide encoding a polypeptide comprising the amino acid sequence of SEQ ID NO: 4 or fragment thereof, wherein the polypeptide has an enzymatic activity to transfer a sulfate group from a sulfate group donor to a hydroxyl group at position 6 of an N-acetylglucosamine residue located at a non-reducing end of an oligosaccharide represented by the formula:

GlcNAcβ1-3Galβ1-4GlcNAc wherein GlcNAc represents an N-acetylglucosamine residue, Gal represents a galactose residue, β1-3 represents a β1-3 glycosidic linkage and β1-4 represents a β1-4 glycosidic linkage.

4. An isolated polynucleotide comprising a nucleotide sequence represented by nucleotide numbers 390 to 1841 in SEQ ID NO: 3.

5. A method of producing a sulfated sugar, which comprises transfecting a cell with the polynucleotide of claim 1; wherein said cell contains an oligosaccharide represented by the formula:

GlcNAcβ1-3Galβ1-4GlcNAc wherein GlcNAc represents an N-acetylglucosamine residue, Gal represents a galactose residue, β1-3 represents a β1-3 glycosidic linkage, and β1-4 represents a β1-4 glycosidic linkage culturing said cell.

6. The method of claim 5 additionally comprising transfecting the cell with a cDNA encoding fucosyltransferase.

7. A method of producing a sulfated sugar, which comprises transfecting a cell with the polynucleotide of claim 2; wherein said cell contains an oligosaccharide represented by the formula:

GlcNAcβ1-3Galβ1-4GlcNAc wherein GlcNAc represents an N-acetylglucosamine residue, Gal represents a galactose residue, β1-3 represents a β1-3 glycosidic linkage, and β1-4 represents a β1-4 glycosidic linkage and culturing said cell.

8. The method of claim 7 additionally comprising transfecting the cell with a cDNA encoding fucosyltransferase.

9. A method of producing a sulfated sugar, which comprises transfecting a cell with the polynucleotide of claim 3; wherein said cell contains an oligosaccharide represented by the formula:

GlcNAcβ1-3Galβ1-4GlcNAc wherein GlcNAc represents an N-acetylglucosamine residue, Gal represents a galactose residue, β1-3 represents a β1-3 glycosidic linkage, and β1-4 represents a β1-4 glycosidic culturing said cell.

10. The method of claim 9 additionally comprising transfecting the cell with a cDNA encoding fucosyltransferase.

11. A method of producing a sulfated sugar, which comprises transfecting a cell with the polynucleotide of claim 4; wherein said cell contains an oligosaccharide represented by the formula:

GlcNAcβ1-3Galβ1-4GlcNAc wherein GlcNAc represents an N-acetylglucosamine residue, Gal represents a galactose residue, β1-3 represents a β1-3 glycosidic linkage, and β1-4 represents a β1-4 glycosidic link culturing said cell.

12. The method of claim 11 additionally comprising transfecting the cell with a cDNA encoding fucosyltransferase.

13. A method of producing a cell containing a sulfated sugar, which comprises transfecting a cell with the polynucleotide of claim 1; wherein said cell contains an oligosaccharide represented by the formula:

GlcNAcβ1-3Galβ1-4GlcNAc wherein GlcNAc represents an N-acetylglucosamine residue, Gal represents a galactose residue, β1-3 represents a β1-3 glycosidic linkage, and β1-4 represents a β1-4 glycosidic link culturing said cell.

* * * * *